United States Patent [19]

Offringa et al.

[11] Patent Number: 5,501,967
[45] Date of Patent: Mar. 26, 1996

[54] PROCESS FOR THE SITE-DIRECTED INTEGRATION OF DNA INTO THE GENOME OF PLANTS

[75] Inventors: Remko Offringa, Leiden; Marcellus J. A. De Groot, Utrecht; Paul J. J. Hooykaas, Oegstgeest; Petrus J. M. Van Den Elzen, Voorhout, all of Netherlands

[73] Assignee: Mogen International, n.v./Rijksuniversiteit te Leiden, Leiden, Netherlands

[21] Appl. No.: 87,928

[22] Filed: Jul. 6, 1993

Related U.S. Application Data

[63] Continuation of Ser. No. 659,288, May 21, 1991, abandoned.

[30] Foreign Application Priority Data

Jul. 26, 1989 [NL] Netherlands .............................. 8901931

[51] Int. Cl.⁶ ........................... C12N 15/82; C12N 15/84; C12N 15/29
[52] U.S. Cl. .................................... 435/172.3; 435/252.2; 435/252.3; 435/320.1; 536/23.2; 536/23.6
[58] Field of Search ............................... 435/172.3, 240.4, 435/240.47, 252.2, 252.3, 320.1; 536/23.2, 23.6; 800/205, 250, DIG. 11, 15, 18, 23, 40, 45, 55, 62

[56] References Cited

FOREIGN PATENT DOCUMENTS 0317509  5/1989  WIPO .

OTHER PUBLICATIONS

Ruvkun, "A general method for site–directed mutagenesis in prokaryotes", Nature 286:85≧88 (1981).
Orr–Weaver et al., "Yeast transformation: A model system for the study of recombination", Proc. Natl. Acad. Sci. USA 78:6354–6358 (1981).
Smithies et al., "Insertion of DNA sequences into the human chromosomal β–globin locus by homologous recombination", Nature 317:230–234 (1985).
Thomas et al., "Site–Directed Mutagenesis by Gene Targeting in Mouse Embryo–Derived Stem Cells", Cell 51:503–512 (1987).
Song et al., "Accurate modification of a chromosomal plasmid by homologous recombination in human cells", Proc. Natl. Acad. Sci. 84:6820–6824 (1987).
Baker et al., "Homologous recombination can restore normal immunoglobulin production in a mutant hybridoma cell line", Proc. Natl. Acad. Sci. 85:6432–6436 (1988).

(List continued on next page.)

Primary Examiner—David T. Fox
Attorney, Agent, or Firm—Morrison & Foerster

[57] ABSTRACT

The present invention provides a method for site-directed integration of DNA-sequences into the genome of plants via homologous recombination, by transforming said plants using the DNA-transfer system of Agrobacterium, in which the transforming DNA comprises in its most simple form a region homologous to the target locus, as well as a region which is different from the target locus either next to one or between two T-DNA borders. Special constructs are provided, which in its most complete form have the following general structure, in which box 1 and 7 represent T-DNA borders, boxes 2 and 6 comprise functional expression cassettes containing negative selection genes, box 3 provides a region of homology with the target locus promoting recombination, box 4 represents a DNA sequence containing a mutation with respect to the target locus, box 5 represents a functional expression cassette containing a positive selection gene, and box E comprises a DNA sequence which is homologous to a region adjacent of the target locus, or in the vicinity of the target locus, which promotes homologous recombination.

19 Claims, 14 Drawing Sheets

OTHER PUBLICATIONS

Capecchi, "Altering the Genome by Homologous Recombination", *Science* 244:1288–1292 (1989).

Kucherlapati et al., "Homologous recombination between plasmids in mammalian cells can be enhanced by treatment of input DNA", *Proc. Natl. Acad. Sci.* 81:3153–3157 (1984).

Wirtz et al., "Recombination of Selectable Marker DNA in *Nicotiana tabacum*", *DNA* 6:245–255 (1987).

Cornelissen et al., "Plastid Transformation: A Progress Report", Chapter 14, *Plant Gene Research: Basic Knowledge and Application, Plant DNA Infectious Agents*, 311–320 (Wien ed. 1987).

Depicker et al., "A Negative Selection Scheme for Tobacco Protoplast-derived Cells Expressing the T-DNA Gene 2", *Plant Cell Reports* 7:63–66 (1988).

Paszkowski et al., "Gene Targeting in Plants", *EMBO Journal* 7:4021–26 (1988).

Paszkowski et al., "Direct Gene Transfer to Plants", *EMBO Journal* 3:2717–22 (1984).

Van den Elzen et al., "A Chimeric Hygromycin Resistance Gene as a Selectable Marker in Plant Cells", *Plant Molecular Biology* 5:299–302 (1985).

Paszkowski et al. 1988. EMBO J 7(13):4021–4026.

Van den Elzen et al. 1985. Plant Mol. Biol. 5:299–302.

Paszkowski et al. 1984. EMBO J 3:2717–2722.

Depicker et al. 1988. Plant Cell Reports 7:63–66.

Cornelissen et al. 1987. pp. 311–320 In: Plant Gene Research: Basic Knowledge and Application, Plant DNA Infectious Agents, Wien, Ed., Springer–Verlag.

Larkins et al. 1985. J. Cell. Biochem. Suppl. 90:264.

Barton et al. 1987. Plant Physiol. 85:1103–1109.

'bordersequence'

5'-AAGCTTTCGGCGAGCTC-GGCAGGATATATTCAATTGTAAAT-CTCGAGCCATGGTCTAGATATC-3'

HindIII SacI XhoI XbaI
Nru I NcoI EcoRV

FIG.6

Oligonucleotides (55 mers) used to construct pSDM3:

```
     EcoRI   BamHI                           BglII                                                    XmaIII
5'-AA TTC TGG ATC CGT GGA GAT CTG | ATT GAA CAA GAT GGA TTG CAC GCA GGT TCT CC-3'
3'-    G ACC TAG GCA CCT CTA GAC | TAA CTT GTT CTA CCT AAC GTG CGT CCA AGA GGC CGG-5'
        phe trp ile arg gly asp leu   ile glu------→NPTII
                                       2    3
                                           BamHI
```

Translational fusions:

```
                                              BamHI
in pNTSSI and 2 : 5'-(SSU 4th exon) -GCC TGG ATC/CGT GGA-(NPTII)-3'
                                     trp ile / arg gly BamHI/BglII
in pNTSS3 and 4 : 5'-(SSU 2nd exon) -CAG GAT C/TG ATT GAA-(NPTII)-3'
                                     asp leu / ile glu
```

FIG.11

PROCESS FOR THE SITE-DIRECTED INTEGRATION OF DNA INTO THE GENOME OF PLANTS

This application is a continuation of application Ser. No. 07/659,288, filed, May 21, 1991, now abandoned.

FIELD OF THE INVENTION

The invention is in the field of recombinant DNA. More in particular, it is related to modified plants, processes for the site-directed modification of the genome of plants, and DNA constructs used therein.

BACKGROUND OF THE INVENTION

During the recent years, techniques have been developed for the genetic manipulation of plant cells and the regeneration of these plant cells into transgenic plants. On the one hand, direct DNA transformation of plant protoplasts may be used for the introduction of the desired DNA into plant cells. For this purpose, several methods are available, e.g. Ca/PEG (Krens et al., 1982; Negrutiu et al, 1987), electroporation and microinjection (Crossway et al., 1986). Using the recently developed microprojectile method (Klein et al, 1987) also intact plant tissues may be transformed with 'naked' DNA. On the other hand, the desired DNA may be introduced into the plant cell using the natural DNA transfer system of *Agrobacterium tumefaciens* and *Agrobacterium rhizogenes* bacteria (for review, see Klee et al., 1987).

*Agrobacterium tumefaciens* and *Agrobacterium rhizogenes*, after attachment to the plant cell wall, are capable of transferring a piece of DNA to the plant cell. Such a piece, the transfer-DNA (T-DNA), is as T-region part of a large plasmid (190–240 kbp) in the bacterium, which is called the Ti-plasmid in the case of *A. tumefaciens* and Ri-plasmid in the case of *A. rhizogenes*. The T-DNA becomes integrated into the nuclear genome of the plant cell (Tomashow et al., 1980; Chilton et al., 1982). Genes residing in the T-DNA are expressed in the plant cell and cause the latter to behave as a tumor cell (Ooms et al., 1981; Willmitzer et al., 1982a+b).

In addition to the genes that are responsible for tumor induction also genes are present on the T-DNA which take care of the production of so-called opines. Opines, like octopine and nopaline, may serve as energy, nitrogen and/or carbon source to Agrobacterium. The enzymes that are needed for the catabolism of these opines are encoded by genes that reside on the Ti- (Ri-) plasmids (e.g. Bomhoff et al., 1976; Kerr and Roberts, 1976; Hooykaas et al., 1977). Depending on the opine production, the Ti- and Ri-plasmids are classified into groups (for example octopine or nopaline plasmids).

The T-region is confined by two imperfect direct repeats of 25 base pairs, also called 'borders' (Yadav et al., 1982; Zambryski et al., 1982; Gielen et al., 1984; Slightom et al., 1985). The presence of these borders in cis is a prerequisite for correct transfer of T-DNA (Wang et al., 1984; Peralta and Ream, 1985).

The presence of the right border is necessary for the efficient T-DNA transfer (Ooms et al., 1982; Shaw et al., 1984b; Wang et al., 1984). Depending on the test system it was found that deletion of the left border in some experiments does (Bakkeren et al., 1989) whereas in other experiments does not lead to a lower frequency of T-DNA transfer to the plant cell (Hille et al., 1983a; Joos et al., 1983). Next to the right border a sequence is present that significantly increases the efficiency of T-DNA transfer (Peralta et al., 1986; Van Haaren et al., 1986, 1987; Wang et al., 1987). The action of this 'enhancer' element is independent on position or orientation with respect to the right border (Van Haaren et al, 1986). From experiments with synthetic borders it appeared that the right and left border sequences are interchangeable and, consequently, the 'enhancer' determines which border sequence becomes the dominant right border (Peralta et al., 1986; Van Haaren et al., 1987).

In addition to the T-DNA, there are virulence genes that on the one hand reside on the chromosome, on the other hand on the Ti-plasmid (Vir-region). These genes are involved in attachment of the bacterium to the plant cell and in the transfer process of the T-DNA to the plant cell (for review see Melchers and Hooykaas, 1987) .

All the gene transfer systems mentioned above have in common the disadvantage that the site of integration of the transforming DNA is unpredictable. Thus, as with the other plant transformation techniques mentioned above, the DNA that is introduced into the plant cell via Agrobacterium appears to become integrated at random locations in the genome (Chyi et al., 1986; Wallroth et al., 1986; Spielman and Simpson, 1986). In certain situations, however, it is desirable or even necessary to determine the site of integration beforehand. Thus, the gene to be introduced might be targeted to a location where the desired regulation of expression is guaranteed. Also the newly introduced DNA could be used to mutate or inactivate a specific plant gene. Several methods have been described to integrate DNA sequences into the plant genome in a site-specific manner. These methods are all based on a mechanism known as homologous recombination.

Homologous recombination is a process that occurs very efficiently within bacteria and yeasts. In these organisms it is used for site-directed integration of newly introduced DNA (Ruvkun and Ausubel, 1981; Orr-Weaver et al., 1981). In yeast it was found that DNA molecules, linearized in the area of homology with DNA integrated into the genome, recombine with a 10–1000 fold higher frequency. More recently, also in mammalian cells homologous recombination between genomic and newly introduced DNA was found to occur (Smithies et al., 1985; Thomas and Capecchi, 1987; Song et al., 1987; Baker et al., 1988; for recent review see Capecchi, 1989). Also in these systems it appeared that upon co-transformation of two defective mutants linearisation of one of the mutants in the region of homology resulted in—on an average—a 10-fold higher recombination frequency (Kucherlapati et al., 1984).

Recombination between two homologous DNA molecules, after their simultaneous introduction into a plant cell, has been reported by Wirtz et al., 1987. European patent application (EP-A-0 317 509) discloses a method for the integration of DNA sequences into the genome of plants through homologous recombination. According to the application the introduction of the DNA construct into the plant host may occur by known techniques, such as the Agrobacterium transfer system. In the Examples, a direct DNA transformation method (with "naked" DNA) was actually used to introduce the incoming DNA into polyethyleneglycol (PEG) treated tobacco protoplasts.

It was stated that modifications on exactly defined locations in the plant genome could be obtained. However, the results of the experiments, using different defective APHII genes, conferring kanamycin resistance, were not conclusive as to whether restoration of the gene occurred on the desired locus ("in situ"). In a later published article on the same experiments by one of the inventors, Paszkowski et al.

(1988), it was only assumed that restoration of the defective APHII gene, due to homologous recombination with the incoming defective;APHII gene, could have occurred on locus, "but further evidence to confirm this was required".

There is still a need for an efficient method for in situ modification of the plant genome and selection of the desired mutants.

SUMMARY OF THE INVENTION

The present invention provides recombinant T-DNA constructs which are useful for the integration of defined mutations in desired locations of the plant genome. The invention further provides DNA-constructs that enable selection of those plants that contain the defined mutations on the desired genomic location. These constructs are especially useful if the integrated mutation is phenotypically difficult to detect. The invention also provides methods to integrate DNA sequences containing defined mutations on desired locations of the plant genome, by introducing these T-DNA constructs to the plant cell using the DNA-transfer system of *Agrobacterium tumefaciens*, or species related thereto. Also vectors are provided, containing said recombinant T-DNA constructs, as well as bacteria transformed therewith. In a further aspect of the invention genetically modified plants are provided, carrying defined mutations in desired locations of their genome, obtained by application of said recombinant DNA construct.

BRIEF DESCRIPTION OF THE DRAWINGS

FIG. 6 shows the sequence of the synthetic HindIII/BamHI fragment containing the left T-DNA border.

FIG. 11 shows the EcoRI/XmaIII fragment used to construct pSDM53.

DETAILED DESCRIPTION

Figure 1:
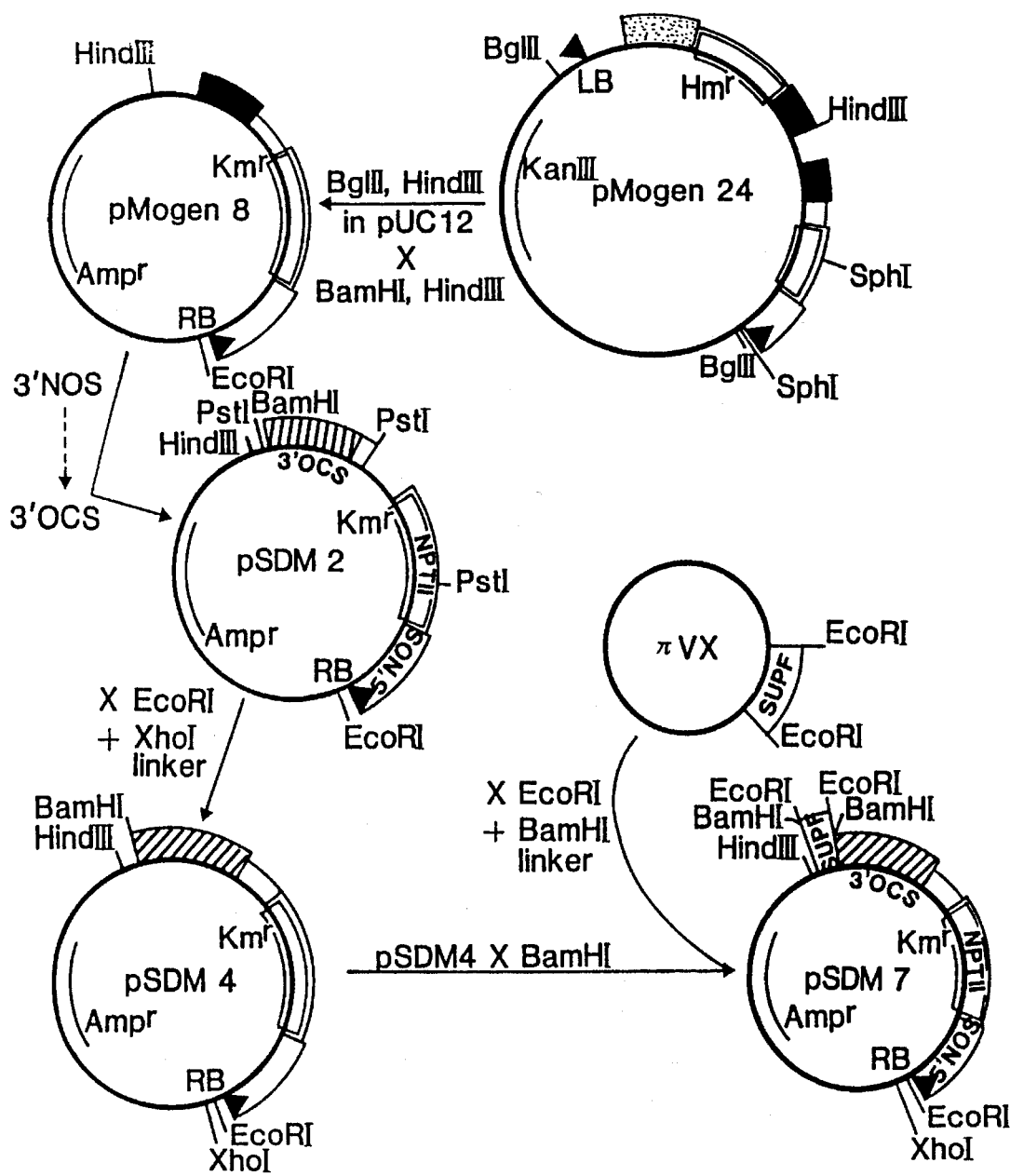
FIG. 1 shows the construction of plasmids pSDM4 and pSDM7.

It was surprisingly found that two T-DNAs, containing regions of homology, which are simultaneously introduced into a plant cell, are physically capable of homologous recombination. Moreover, newly introduced T-DNA, hereinafter referred to as the 'targeting construct', containing regions of homology with the plant genome of the acceptor plant cell was also found to be capable of recombination with the genomic DNA sequence, within the regions of homology. In some cases the restored phenotype, viz. kanamycin resistance, was shown to be the result of restoration of the mutated locus, i.e. the plant had been modified in situ, on the desired locus in the genome. The desired locus will also be indicated hereafter as 'target locus'.

The recombined sequences in the plant genome appeared stable and genetically inheritable.

The frequencies of recombination (compared with the number of transformants) found by us for the Agrobacterium system are comparable with the frequencies that were found by Wirtz et al., (1987) and by Paszkowski et al., (1988) for the direct DNA-transformation method, using naked DNA.

The possibility to use the Agrobacterium transfer system to enforce homologous recombination in plant cells was quite unexpected, in the light of the structural properties of T-DNA, and the involvement of proteins in the transfer proces. This is illustrated by the following findings;

a) using the Agrobacterium transfer system, the transforming DNA (T-DNA) is excised from the transforming plasmid at the T-DNA borders, and consequently, is not linearized within a region of homology with the target locus, as is the case with all naked DNA, b) unlike with naked DNA, the T-DNA molecule was not expected to be available for homologous recombination due to its single-stranded nature and as a consequence of the association with virulence proteins such as Vir E (Gietl et al., 1987; Das, 1988; Sen et al., 1989; Citovsky et al., 1988, 1989; Christie et al., 1988) and Vir D2. VirD2 is even known to be covalently attached to the 5' end of the so-called T-strand (Young and Nester, 1988; Herrera-Estrella et al., 1988; Ward and Barnes, 1988). A model is described in which the T-DNA is transferred to the plant cell as a single stranded linear molecule (Stachel et al., 1987; Albright et al., 1987) and in which single stranded-DNA binding proteins possibly protect the DNA from nuclease activity before integration into the genome (Gietl et al., 1987; Citovsky et al., 1988, 1989; Das et al., 1988; Sen et al., 1989; Christie et al., 1988; Young and Nester, 1988; Herrera-Estrella et al., 1988; Ward and Barnes, 1988).

c) the very high background that is to be expected, due to the very efficient random integration of T-DNA; this requires a rigorous selection mechanism to find plant hosts with the proper integration (i.e. via homologous recombination) in situ, while discarding the non-transformed hosts, as well as the overwhelming majority of the plant hosts having undesired random integrations of the entire T-DNA in their genome. Especially, when the desired mutations to be integrated into the plant genome are difficult to observe immediately (i.e. that have a phenotype that can not easily be observed or screened for), this poses a serious problem. In fact many in situ modifications are difficult to detect.

Although it was mentioned that Agrobacterium can be used as DNA-transfer system to direct homologous recombination, until now, no results had been reported, which is supporting the above mentioned doubts with respect to the suitability of the Agrobacterium DNA-transfer system for the site directed mutagenesis of the plant genome.

Some of the advantages of the use of Agrobacterium as a DNA-transfer system to enforce site-directed mutagenesis of the plant genome over the use of naked DNA transformation, are, among others:

1) Protoplasts are transformed by Agrobacterium with a considerably higher frequency than is possible when using naked DNA transformation. From calli that were regenerated from protoplasts of *Nicotiana tabacum* cv. petit havana SR1, cocultivated with Agrobacterium during 72 hours, 20–50% appeared to be transformed (Van den Elzen et al., 1985a; Depicker et al., 1985). Even if the recombination frequency with T-DNA would be lower than the recombination frequency with naked DNA, the percentage of cells that is transformed by homologous recombination could be higher due to a higher transformation frequency using the Agrobacterium DNA-transfer system.

2) Regeneration of protoplasts into plants is still a problem for many plant species. This limits the use of 'naked' DNA-transformation, with which it is necessary to work with protoplasts (except for the particle bombardment technique, which may use regenerable plant parts, however this technique causes a lot of scrambling, and for this reason appears not very useful for this purpose). Furthermore, regeneration of protoplasts into plants proceeds through a callus phase. During such a phase somaclonal variation is often observed. Somaclonal variation includes all chromosomal rearrangements in mitotically dividing tissue and results in chimaeric tissue. To obtain transformed plants via Agrobacterium, no regeneration of protoplasts is needed. Easily regenerable tissues of the plant like e.g. leaf discs (Horsch et al., 1985), potato tuber discs (Sheerman and Bevan, 1988) or meristems (Ulian et al., 1988) can be used to provide transformed plants after cocultivation with Agrobacterium. Shoots can also be regenerated with reasonable frequency from leaf discs of tobacco plants that have been inoculated with *A. rhizogenes*. Easily regenerable plant tissue, that can be readily transformed using Agrobacterium, can now be obtained from many other plant species as well.

3) In contrast with integration of naked DNA, the integration of the T-DNA is precise. With this is meant that T-DNA copies often integrate intact and that 'scrambling' hardly occurs (Hain et al., 1985; Czernilofsky et al., 1986; Deroles and Gardner, 1988). Wirtz et al. (1987) and Paszkowski et al (1988) find rather complex integration patterns in the plant genome, in their experiments, where they use naked DNA-transformation to examine homologous recombination.

4) Some naked DNA-transformation methods require so-called carrier-DNA to increase the transformation frequency. This carrier DNA might interfere with the homologous recombination event. Besides, this carrier DNA becomes more or less randomly integrated into the plant genome (Peerbolte et al., 1985) and, consequently, causes undesired mutations in the genome of the host. The Agrobacterium system does not require carrier-DNA.

The attention for the Agrobacterium system further increased after it appeared that in addition to dicotyledonous plants also monocots—among which bulbous plants, asparagus and cereals—can be transformed using Agrobacterium (Hooykaas-van Slogteren et al., 1984; Hernalsteens et al., 1984; Graves and Goldman, 1986, 1987; Grimsley et al., 1987).

In general it was found that two T-DNAs are capable of homologous recombination within the plant cell. In particular this was shown for a model gene namely the NPTII-gene, conferring kanamycin resistance ($Km^r$). The NPTII gene is derived from the bacterial transposon Tn5 (Beck et al., 1982) and codes for the enzyme neomycin phosphotransferase. When the NPTII gene is placed under regulatory signals derived from plant genes (or Agrobacterium T-DNA genes), it can be expressed after introduction in the plant cell and provide resistance to the antibiotic kanamycin (Bevan et al., 1983; Herrera-Estrella et al., 1983). Plant cells are sensitive to kanamycin. Therefore, the gene can be used as a selectable marker for transformed cells or tissue slices. This $Km^r$ gene is chosen as model gene for the detection of homologous recombination in plant cells, viz. protoplasts of *Nicotiana tabacum* cv. petit havana SR1.

Upon separate transformation of T-DNAs containing a defective NPTII gene, no $Km^r$ protoplasts could be obtained. However, simultaneous introduction of both defective NPTII-genes by cocultivating tobacco protoplasts with two different *Agrobacterium tumefaciens* strains, each containing a different defective NPTII-gene in a binary vector, resulted in $Km^r$ tobacco cells. These cells could be regenerated into $Km^r$ calli and subsequently, into $Km^r$ plants. Analysis at the DNA level confirmed that both defective NPTII-genes complemented each other through homologous recombination. Analysis at the protein level also showed the recombination event had occurred at exactly the correct site within the coding region of the gene. The possibility that the recombination event had taken place in Agrobacterium was excluded by control experiments.

This shows, for the first time, that homologous recombination in a plant cell between two T-DNAs sharing a region of homology is possible.

In another experiment, a transgenic tobacco plant, containing a defective NPTII gene in its genome was transformed with a repair construct that was introduced into the plant cell using the Agrobacterium DNA-transfer system. The repair construct also contained a defective NPTII-gene mutated at a different location within the gene. It was shown that the mutation could be restored due to homologous recombination between the newly introduced NPTII mutant in targeting construct and the mutant NPTII gene residing in the plant genome. Again, recombination had occurred correctly, resulting in a restored gene, encoding a fully active NPTII-enzyme, that is identical to the wildtype NPTII product. Most importantly, analysis at the DNA level revealed that recombination had occurred at the target locus, resulting in restoration of the gene in situ.

In other experiments it has been shown that targeting is also possible to sequences naturally occurring in the plant genome (endogenous sequences).

In these experiments an endogenous gene, viz. a member of the rbc SSU multigene family, was selected as target locus to investigate the possibility to mutate endogenous sequences in situ via homologous recombination. Genes of this family code for the small subunit of ribulose-1,5-biphosphatecarboxylase/oxygenase (rbcS), a nuclear encoded chloroplast localized protein involved in photosynthesis. Expression of the SSU genes is light-dependent.

Figure 10:
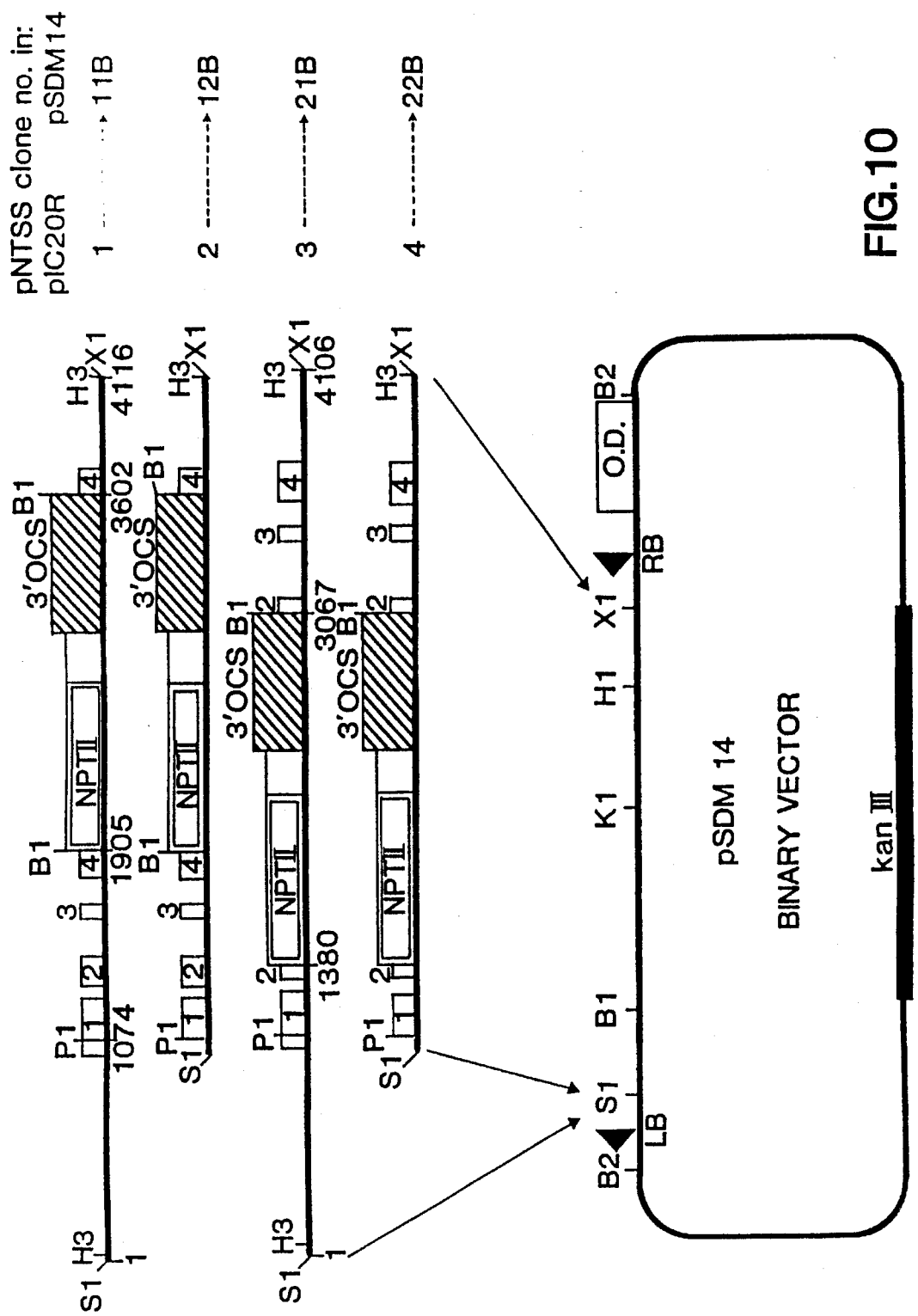
FIG. 10 shows the translational SSU-NPTII fusion constructs.
Figure 12:
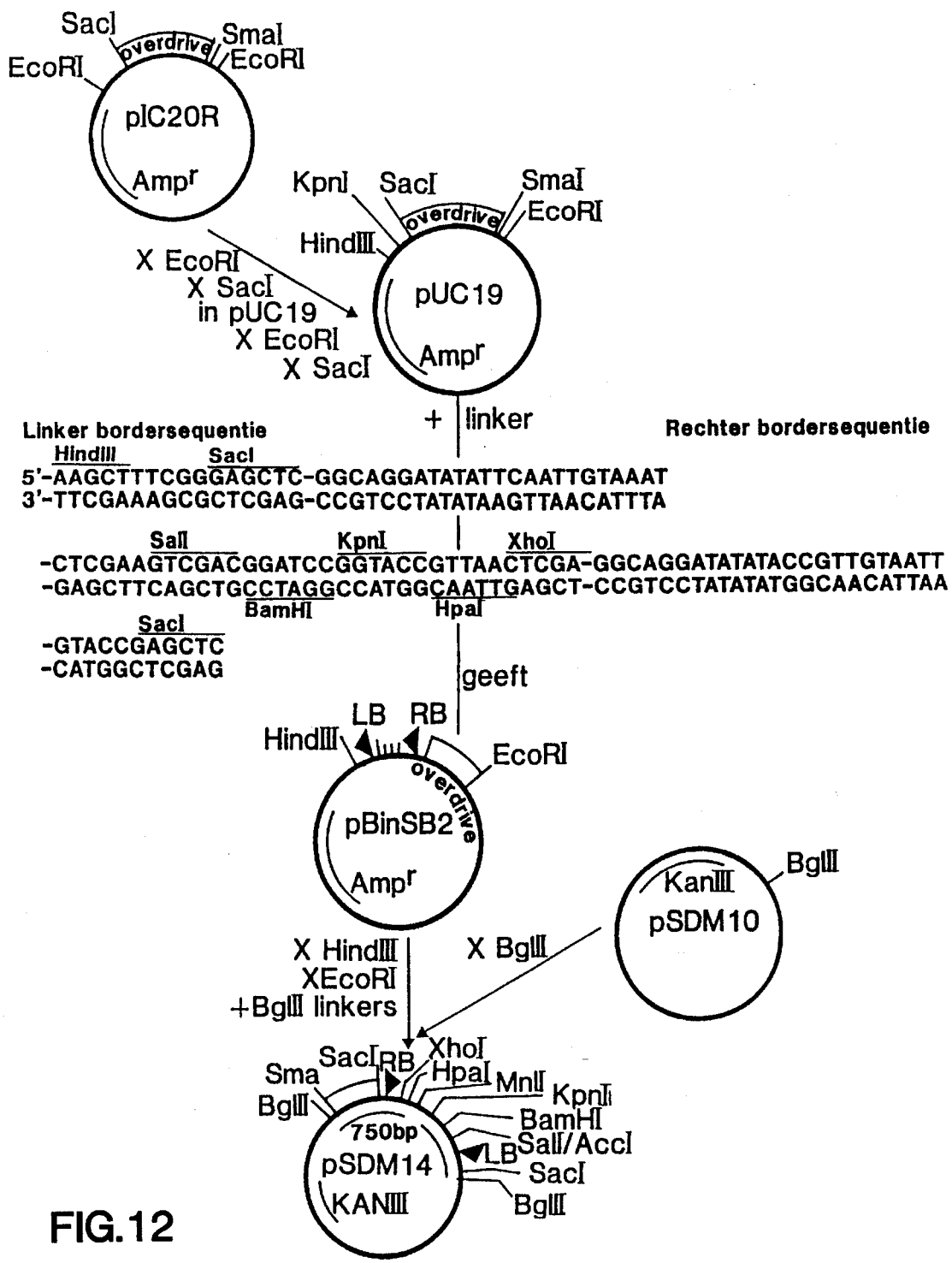
FIG. 12 shows the construction of the binary vector pSDM14.

Therefore two targeting-constructs were made, each comprising a different translational fusion between the coding region of this rbcS gene, consisting of four exons and the coding region of the NPTII gene (see FIG. 10). One chimaeric gene, a translational fusion in the second exon of rbcS, codes for a protein in which the transport peptide (involved in targeting the rbc gene product to the chloroplast) and the first 23 amino acids of the mature SSU protein are fused N-terminally to NPTII. A similar fusion protein between the transport peptide and the first 23 amino acids of the mature protein of the rbcS gene from pea and NPTII has already been described and appeared functional (Schreier et al., 1985). The other fusion gene codes for a protein in which the transport peptide and 99 amino acids of the mature SSU protein of the N-terminus of the NPTII enzyme are fused. Up to 0.01% of the transformed calli appeared km$^r$, which in most cases appeared light-regulated, whereby some of the SSU-NPTII fusion protein appeared transported to the chloroplast. Analysis of the genomic locus at the DNA level, using Southern blotting and PCR (Polymerase Chain Reaction) analysis, revealed that the light-regulated Kanamycin resistance of part of the transformed calli, indeed resulted from modification of the target locus in situ, i.e. at the selected rbcS locus.

The results of this experiment prove, that desired mutations can be introduced in desired loci in the plant genome, independent of the fact whether the target-locus consists of a DNA sequence that is exogenous or endogenous, via homologous recombination, using T-DNA constructs. Furthermore, it nicely illustrates, that any functional part of a gene or an entire gene, which is functional in combination with a functional part of any other gene residing in a selected target locus of the genome of the plant host may be correctly fused to that part in situ, via homologous recombination between the targeting construct and the target locus, resulting in a functional fusion of the two functional gene parts. In its broadest perspective, the present invention provides a method for manipulating in principle any part of the plant genome, without changing the location of that part of the genome.

In the experiments mentioned above, the homologous recombination events could be readily detected, since the gene fragments sharing homology were able to complement each other, thereby conferring kanamycin resistance to the host. However, in many cases, the mutation one wants to introduce into the plant genome via homologous recombination, can not be selected for directly. For instance mutations such as exchange of amino acids or altering codon usage of genes and the like, may not be readily detectable, and thus have to be analysed on the DNA level. Such analyses may involve, restriction mapping of the genomic DNA, PCR-analysis, and/or DNA-sequence analysis.

Since, in these cases, it is very awkward, time consuming and expensive to screen all coincubated cells for the desired recombination event on the DNA-level, it is desirable to be able to select for transformed hosts, using a positive selection marker, such as an antibiotic gene or a herbicide resistance gene and the like, which have a high probability of being transformed through homologous recombination instead of random integration at undesired locations in the genome. Since the random integration frequency is known to be far greater than the frequency of homologous recombination, a strong selection mechanism is required to discard all those cells that have been transformed through random integration. Therefore, it is preferred, according to the invention, that a positive selection gene is used in combination with a negative selection gene, optionally two negative selection genes, residing in the targeting construct, outside the regions involved in the homologous recombination event. The general structure of such a T-DNA construct is outlined in FIG. 14A. The boxes 1 and 7 each represent T-DNA borders, boxes 2 and 6 are expression cassettes containing a negative selection gene, box 3 and 4 contain sequences used for recombination and mutation of the target locus, and box E contains sequences involved in recombination outside the target locus. The negative selection genes serve to provide disadvantage (preferably lethality) to the cells that have these genes integrated in their genome in an expressionable fashion (e.g. in an expression cassette, containing the structural gene between the regulatory regions that are required for proper expression in the plant host).

Accordingly, all cells having the entire T-DNA randomly integrated in the genome will be harmed or killed, due to the presence of the negative selection genes. Only those cells will survive that have the positive selection gene integrated in their genome, while the negative selection genes have been discarded as a consequence of recombination within the regions of homology. Since scrambling of T-DNA is known to occur at a considerably lower rate as compared to naked DNA, the combination of a positive selection gene inside the regions of homology, and one, optionally two, negative selection genes outside the regions of homology, has special advantage if used in combination with the Agrobacterium DNA-transfer system. However, it may very well work with naked DNA too.

Since the property of intact integration (lack of scrambling) will probably be connected with the fact that T-DNA is packed with proteins, this system might also work with T-DNA packaged in vitro, as well as with naked DNA of other origin than Ti/Ri vectors, that has been packed with DNA-binding proteins.

In accordance with the invention it is highly preferred if the construct contains two T-DNA borders in their most active orientation. However it is known in the art that one T-DNA border is sufficient for DNA transfer, and also borders can be used which are synthetic or are integrated in the opposite orientation with respect to the wildtype situation.

The choice of the positive selection gene (contained in box 5) is not critical with respect to the invention as long as it is functional in the host, and administered to the plant host in an expressionable fashion. The positive selection gene may be chosen from the group including (but not limited to) NPTII-gene (encoding resistance for kanamycin), HPT-gene (hygromycin resitance), the ALS gene (chlorsulphuron resistance), DHFR-gene (methothrexate resistance). In order to express these genes, strong constitutive promoters may be used, such as the 35S, or the 19S promoter derived from the cauliflower mosaic virus (CaMV), T-DNA promoters from Agrobacterium, but also plant promoters, or any promoter which is functional in the host. In general it is preferred that the DNA-sequences not meant to be involved in homologous recombination do not have homology with DNA sequences residing in the genome of the plant. However in case this is required, the regions of homology not meant to participate in the recombination event should be kept as small as possible, in order not to interfere with the desired recombination event.

The choice of the negative selection gene (contained in box 2 and/or box 6) is not critical to the invention as long as it is functional in the plant host, and administered in an expressionable fashion. The negative selection gene may for instance be chosen from the group consisting of aux-2 gene from the Ti-plasmide of Agrobacterium, the TK-gene from SV40, cytochrome f450 from *Streptomyces griseolus*, the Adh-gene from Maize or Arabidopsis, but any gene encoding an enzyme capable of converting harmless substances into harmful substances may be used.

Parts 3 and 4 of the targeting construct are most critical with respect to the invention.

In a first preferred embodiment of the invention, mutations are introduced in a selected locus (hereinafter called the target locus) requiring that the remainder of the sequence of the target locus (i.e. on both site of the mutation to be introduced) must be kept intact. Therefore, the sequence immediately next to the mutation must also be provided in box 4 of the construct. Thus, mutations may be introduced inside functional genes, or functional parts of genes, such as regulatory regions, signal sequence, sequences encoding parts (such as functional domains) of the mature protein, or even introns, as well as other functional target loci, not necessarily encoding protein, without changing the sequence of the target locus contiguous to the mutation. In this situation both box 3 and box 4 will have homology with the target locus, whereby box 3 serves to promote the homologous recombination event, and is therefore indicated hereinafter as the recombination box, whereas box 4 comprises the mutation as well as the sequences of the target locus that should not be changed, indicated hereinafter as the complementing box. Since the complementing box can only be integrated into the target locus after homologous recombination within the recombination box, the probability of a recombination event within the latter box should be favoured. It is well known that the longer the region of homology the larger the probability of recombination in this region. It is therefore preferred, that the recombination box be sufficiently long to promote homologous recombination, and furthermore, that it be significantly longer than the complementing box. It should also be understood that if the recombination box of the construct represents the upstream (5') region, the complementing box constitutes the downstream (3') region of the target locus, and vice versa. Furthermore box 3, 4, and E should have the same 5'to 3' orientation.

Most importantly, the order of boxes 3, 4, 5, and E can not be changed in this embodiment of the invention, although the entire fragment may be inserted in the opposite orientation with respect to the T-DNA borders. Likewise, also the entire fragment including the negative selection markers may be inverted with respect to the T-DNA borders.

In the constructs, the complementing box may carry three kinds of mutations, which per definition are located immediately next to the recombination box. These mutations comprise insertion of basepairs, which may be from one to several thousands of basepairs, a replacement of basepairs, not changing the number of basepairs of the target locus, or a deletion of basepairs reducing the number of basepairs, which may be 1 basepair or as much as several thousands of basepairs of the target locus, or combinations of these.

It should be understood that the recombination box in the construct does not necessarily have to start at the precise beginning of the target locus as it is defined. It might as well begin before or after the start of the target locus. However, per definition, it ends exactly at the point where the mutation of the target locus must begin. The complementing box, per definition, starts exactly with the first nucleotide of the mutation, in the case the mutation is an insertion or a replacement, but does not necessarily have to end at the last nucleotide of the target locus, although also per definition, it includes the last nucleotide of the target locus. In the case the mutation constitutes a deletion of basepairs, the complementing box begins exactly where the deletion ends. Of course, the complementing box may contain more than one mutation, even more than one type of mutation. If, in this case, the number of bases separating the the different mutations is large with respect to the regions of uninterrupted homology, it is preferred that such mutations are integrated into the plant genome one after the other, i.e. in different transformation experiments.

In principle, an entire expressible gene may be inserted into the target locus, which gene may itself provide a selectable or screenable trait. In this case box 5, representing an expressible positive selection gene, may be absent in the construct. Consequently, the need for a region of homology outside the target locus (box E) is also lost.

In a second preferred embodiment of the present invention, box 4 may represent a sequence that is entirely non-homologous with respect to the target locus. Thus, it may be an exogenous sequence with respect to the host, for instance a sequence derived from a different variety of the same plant species, a different plant species, an organism other than a plant, a synthetic sequence, or a genetically manipulated exogenous sequence, but also a sequence that is endogenous to the plant host, derived from a different locus of the host genome. In the latter case the chances of undesired homologous recombination should be minimized by reducing the length of box 4 with respect to box 3. As for the situation mentioned above, box 5 may be absent if after recombination a selectable or screenable trait arises, eliminating the need for an additional selection gene and box E.

In a third embodiment of the invention, the site directed mutagenesis of the genome merely aims at total inactivation of functional genomic regions. These functional regions include, but are not limited to, genes, regions involved in regulation of gene expression, DNA replication, and the like. Inactivation may be achieved by creating deletions inside the target locus, replacements (e.g. introduction of stopcodons) or insertions (e.g. causing frameshifts and the like), using any of the constructs mentioned above. It will appear to an expert, that in those cases the inactivation of the target locus can be selected or screened for directly due to the apparent phenotype of the target locus, there will be no need to provide for positive nor negative selection genes. The construct may just contain box 1, 3, 4, and 7, in which box 4 may contain any kind of mutation that is suitable to inactivate the target locus.

Figure 14A:
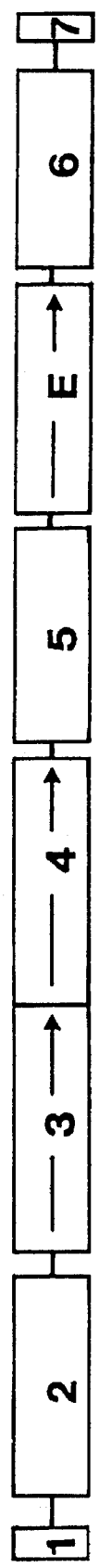
FIG. 14A shows a consensus for T-DNA replacement constructs that can be used to achieve gene targeting.
Figure 14B:
FIG. 14B shows a consensus for T-DNA insertion constructs that can be used to achieve gene targeting.

A somewhat different targeting construct, indicated as 'insertion vector' is depicted in FIG. 14B. In addition to the construct outlined in FIG. 14A, this construct may be used to introduce insertions (box I) into the target locus. Here, Box 3 and 4 represent DNA sequences homologous to the target locus, in which the basepair sequences of the boxes still have the same 5' to 3' order as in the target locus, but the entire boxes changed places with respect to the situation in the target locus. A functional alternative of the construct depicted in FIG. 14B is one in which both box 3 and 4 point to the other side.

Although targeting of endogenous DNA sequences is exemplified using a target construct in which the promoter and part of the leader sequence of the small subunit of the ribulosebisphosphate carboxylase (rbcS) gene are comprised in the recombination box, it will appear to an expert that in principle any part, whether belonging to the regulatory elements of a gene, the coding regions of a gene, or any other sequence of any gene, gene fragment or different DNA-sequence, may be used in the recombination box in the targeting construct, in order to promote homologous recombination. To put it differently, any part of any gene or any other DNA sequence may be mutated in an exactly defined manner, provided the DNA sequence of the regions immediately flanking the site to be mutated is sufficiently known, using a construct as depicted in FIG. 14A. The invention is not restricted to loci of which the DNA sequence is known, since the availability of new DNA-sequences is just a matter of time.

Although the invention is exemplified with tobacco protoplasts and plants, also protoplasts from other species can be transformed using this method, both monocotyledonous and dicotyledonous, as well as other parts of plants or tissues, e.g. tuber-discs, leaf-discs, embryos, pollen, meristems, and the like, as long as they can be transformed with the Agrobacterium transfer DNA-system. Plant groups of special interest in the light of this invention include but are not limited to the Solanaceae, Leguminosae, Umbelliferae, Cruciferae, Compositae, Alliaceae, Vitaceae, Compositae, Asparagaceae, Chenopodiaceae, Liliaceae, Orchideaceae, Theaceae, Coffea, Cucurbitaceae, and the like.

In principle, the naturally occurring DNA-transfer system of Agrobacterium could be used to practice the invention, but the size of the wildtype Ti- and Ri-plasmids hampers the manipulation of the T-DNA using recombinant DNA techniques. Therefore, modified Agrobacterium vector systems are used in genetic engineering of plants. The plasmids that are subject to genetic manipulation have been trimmed to a more convenient size. With these so-called cointegrate vectors, the foreign DNA (whether or not next to one, or between two borders) can, via small plasmids that are capable of replicating in E. coli, be brought onto the Ti- or Ri-plasmid by means of homologous recombination (Hille et al., 1983b; Barton and Chilton, 1983; Zambryski et al., 1983; Deblaere et al., 1985; Fraley et al., 1985).

Especially preferred in accordance with the invention is the so-called binary vector system, in which the T-region is carried by the binary vector, a plasmid which is capable of replicating in both E. coli and A. tumefaciens, while the Vir-region resides on a helper Ti- or Ri-plasmid (De Framond et al., 1983; Hoekema et al., 1983; Hoekema et al., 1984a). The T-region now only contains border sequences between which the genes that are to be transformed can be cloned. Hereby the enhancer element is present next to the right border.

Also when the T-DNA is located on the chromosome of Agrobacterium it can be transferred to the plant cell, provided that the virulence genes are present in trans in the same bacterium (Hoekema et al., 1984a).

When Ti- or Ri-plasmids are introduced into bacteria that are related to Agrobacterium, such as Rhizobium (Hooykaas et al., 1977) or Phyllobacterium (Van Veen et al., 1988), then the T-region of these plasmids appears still to be transferred to the plant cell, upon coincubation.

The system of Agrobacterium-mediated gene-targeting may be applied, among others, for the in situ modification of genes of interest in the field of human nutrition, food-processing, animal-fodder, industrial non-food applications and plant genes related to environmental fitness.

The in situ modifications of genes may affect any aspect of gene functioning, regulation of gene expression, or protein functioning.

Affecting gene functioning includes any mechanism of complete inactivation of genes (including members of multigene families or other sequences) the expression of which is not desired. Such genes may be encoding key-enzymes in metabolic pathways, such as fatty acid-, carbohydrate-, or secondary pathways. Inactivation of such genes may cause specific alteration of these metabolic routes. Such alterations may be desirable as to inhibit the formation of metabolites that are unhealthy (such as specific alkaloids, and the like) untasty, or otherwise undesirable. It may be very advantageous to inactivate genes that are involved in fruit ripening, flowering, pollination, and the like. Also genes may be inactivated in plants that are used as raw material in food processing, production of food ingredients, pharmaceuticals, or for industrial use and the like.

The invention is also very useful for the inhibition of the formation of proteins or polypeptides that are themselves undesired, for instance those that are toxic to humans, domesticated animals and cattle, and the like.

Regulation of gene expression

In a slightly different embodiment of the invention genes of interest may not be entirely inactivated, but their regulation of expression modified. Such modifications may involve non-modulated stimulation of expression (overexpression), (partial) inhibition of expression, responsiveness to certain internal (hormones, metabolites) or external (heat, cold, drought, light-intensity, day-length, tactile stimuli, chemicals, pathogens) signals. For purposes of simplicity regulation of gene expression includes also protein-sorting (transport of proteins to specific compartments of the cell, or the extracellular space). It is known that certain DNA sequences are involved in non specific stimulation or inhibition, other sequences in responsive stimulation or inhibition of gene expression. Many of such sequences such as regulatory elements (including promoters, transcription and translation enhancers, light-responsive elements, and the like), sequences coding for signal peptides, organelle import domains, transit peptides and the like are known in some detail, and many more will come at hand in the near future. It has been established that many of such sequences constitute a functional domain of itself (i.e. functioning irresponsive of other functional domains), which creates the possibility to combine hitherto nonexisting combinations of domains, thus altering regulation ad libitum. However, it seems that genomic localisation may play a significant role in the regulation of newly introduced gene-constructs as well, sometimes completely overruling other factors affecting gene regulation. Sometimes, genes can not be expressed in a specific plant host at all. This is one of the major problems in genetic engineering of plants. The present invention may help to solve this problem in creating the possibility to target newly introduced gene-constructs to genomic loci that have a somehow predictable expression mode. For instance, genes that need overexpression can be targeted now to genomic loci that are known to be very active. In order to achieve this highly active loci can be chosen such as the loci on which some of the rbcS genes, the chlorophyll a/b binding protein genes, and the like, are located. The DNA-sequences of interest may be introduced with or their own regulatory elements, such as promoters, enhancers, transcription terminators and the like, or fused to the regulatory elements present in the target locus.

The problem of poor expression also plays a role when one Wants to alter the structure of endogenous genes, as to modify protein structure, or domains involved in routing, without changing the genomic location. Formerly, such genes were isolated and modified in vitro, and subsequently reintegrated into the plant genome using standard transformation techniques. By doing so, the altered gene-construct reintegrates randomly into the plant genome, often losing its specific regulation. Using methods provided for by the present invention, the gene can now be modified in situ, with little chance to abolish its mode of expression.

For the example, the amino acid content of the encoded protein can be changed by insertion, deletion and/or substitution of amino acids following replacement of some or all of the basepair sequence encoding for the protein. Genes of particular interest are genes coding for abundant proteins like seed storage proteins such as zein, napin, phaseolin, storage albumin and the like, of which the nutritional value can be raised by introducing more essential amino acids, such as lysine or tryptophane.

Furthermore, the invention can have considerable advantage when used for the in situ modification of proteins involved in some form of environmental stress. These genes often have a very intricate mode of gene regulation which one might not want to disturb by changing the genomic location of the gene, although it might be advantageous to change the protein itself. For instance the mode of action, stability or pathogen range of a particular protein can be changed.

On the other hand mutations may be introduced into a gene of interest expressly causing altered gene expression at the protein level. This may be achieved for instance by altering codon usage. These mutations can be introduced using techniques very well known in the art.

The following figures illustrate the invention.

Figure 2:
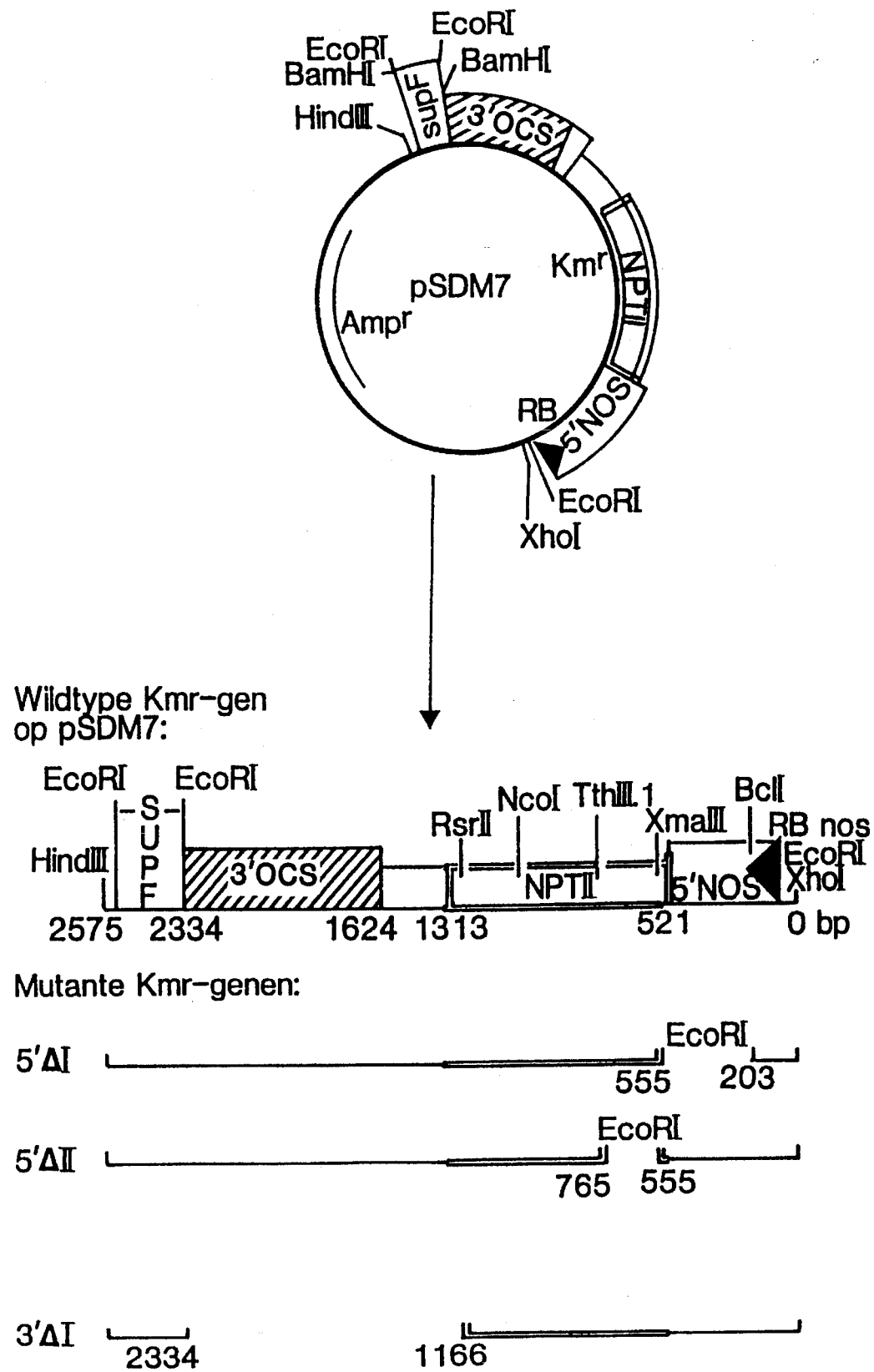
FIG. 2 shows the construction of the defective $Km^r$ genes starting from plasmid pSDM7.
Figure 3:
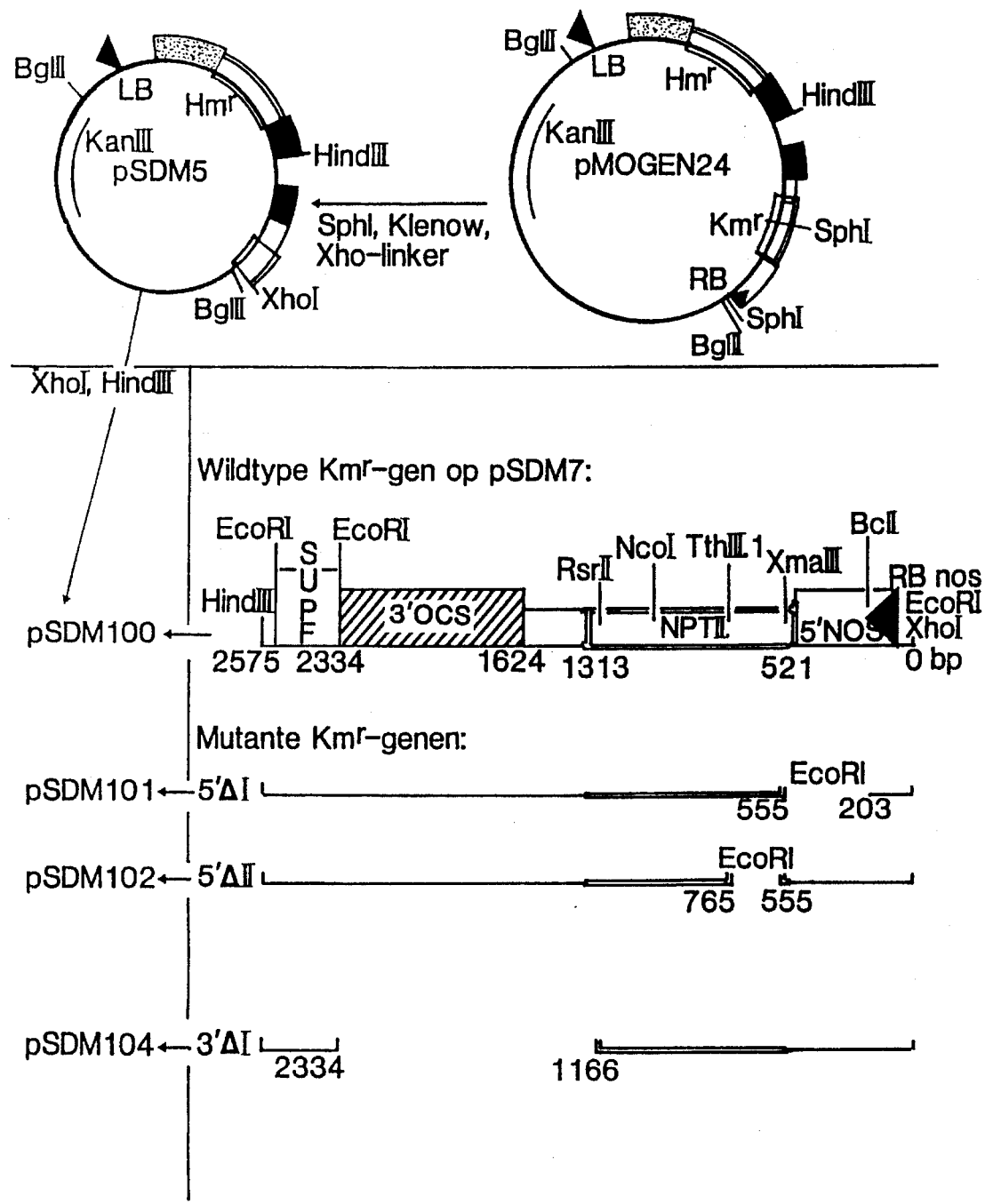
FIG. 3 shows the cloning of the defective $Km^r$ genes into the binary vector pSDM5.
Figure 5:
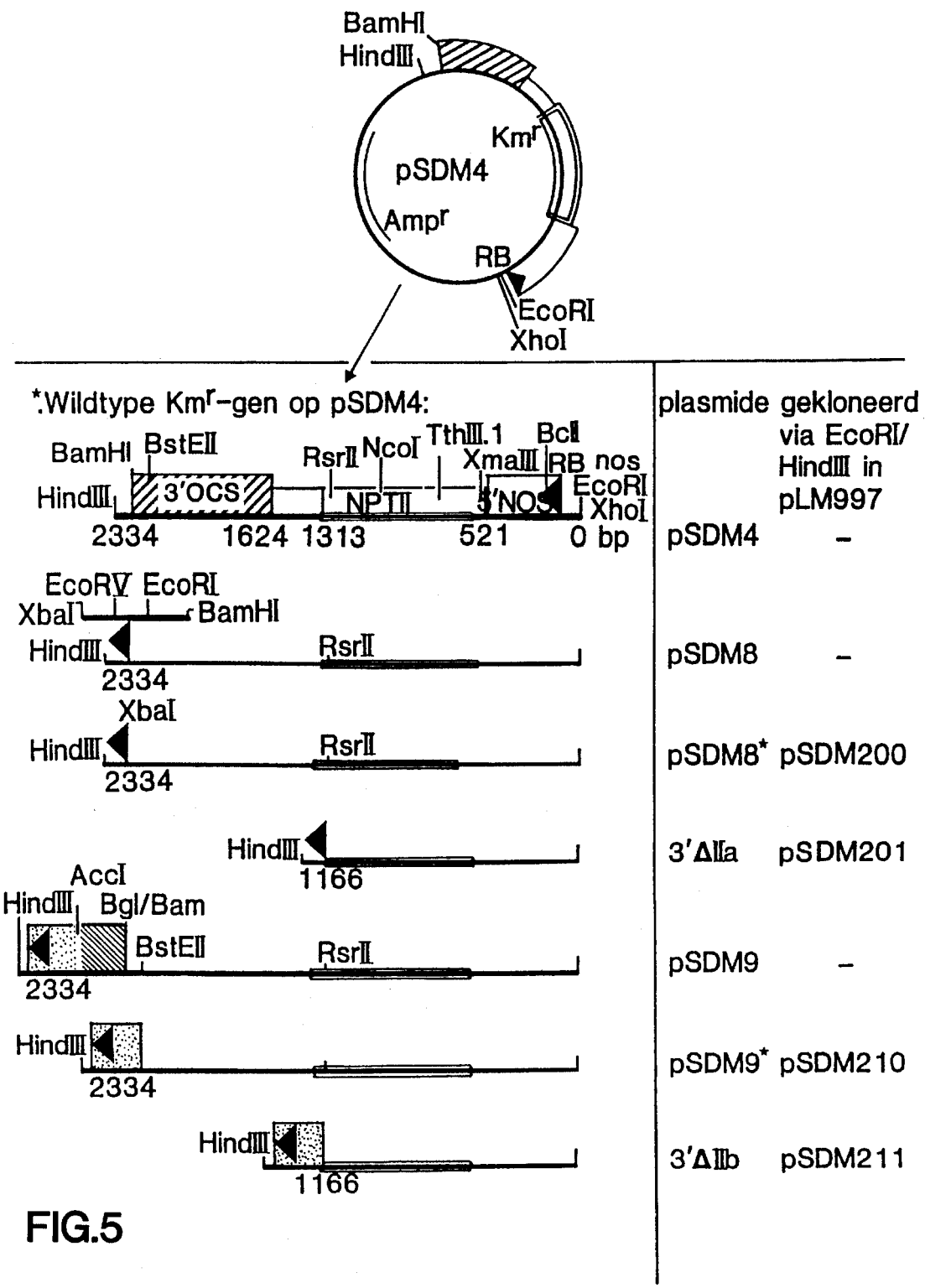
FIG. 5 shows the construction of the 3' deletion mutants of the $Km^r$ gene starting from plasmid pSDM4.

FIG. 1:

Construction of plasmids pSDM4 and pSDM7, which contain the intact Km$^r$ gene that is functional in plant cells. These plasmids served as basis for the construction of the different defective genes (FIGS. 2, 3 and 5). The following cloning steps are depicted here: 1) the transfer of the BglII/HindIII fragment from pMOGEN24 to pUC12 (xBamHIxHindIII), 2) the replacement of the transcription terminator of the nopaline synthase gene (3'NOS) with that of the octopine synthase gene (3'OCS), 3) the introduction of a 8 bp synthetic DNA fragment (linker) containing a XhoI restriction site at the EcoRI restriction site and 4) the transfer of the supF containing fragment from plasmid πVX to the BamHI site of pSDM4. Abbreviations and symbols are explained in the legend.

FIG. 2:

Construction of the defective Km$^r$ genes 5'▲I, 5▲II and 3'▲I starting from plasmid pSDM7. The intact Km$^r$ as it present on pSDM7 is depicted linear. Beneath it the defective genes are depicted with lines. The lines indicate which DNA sequences of the intact Km$^r$ gene from pSDM7 are still present in the defective genes. The 5'▲I was obtained by replacing the XmaIII/BclI fragment, after filling in with Klenow-polymerase, with an oligonucleotide of 10 bp, on which an EcoRI site (EcoRI-linker) is located. Replacement of the the TthIII.1/BclI fragment after filling in with Klenow-polymerase, with an EcoRI-linker (10 bases) resulted in 5'▲II. In 3'▲I the 3' region of the Km$^r$ gene till the RsrII site was removed. The supF gene was cloned distal from the mutant Km$^r$ gene. Abbreviations and symbols are explained in the legend.

FIG. 3:

Cloning of the defective Km$^r$ genes (see FIG. 2) as XhoI/HindIII fragment into the binary vector pSDM5 (xXhoI x HindIII). In this way the defective genes were located next to the Hm$^r$ gene between the T-DNA border sequences (see FIG. 4). The plasmid pSDM5 was derived from pMOGEN24 by replacing the SphI fragment of pMOGEN24, after blunt-ending with Klenow-polymerase, with a XhoI-linker (10 bp synthetic DNA fragment containing a XhoI restriction site). See also legend.

FIG. 4:

Overview of the T-region of plasmid pSDM100 on which the intact Km$^r$ gene is located. Beneath it, with black lines is indicated which DNA-sequences of the T-region of pSDM100 are also present in the T-region of pSDM102 and in that of pSDM104. See also legend.

Figure 7:
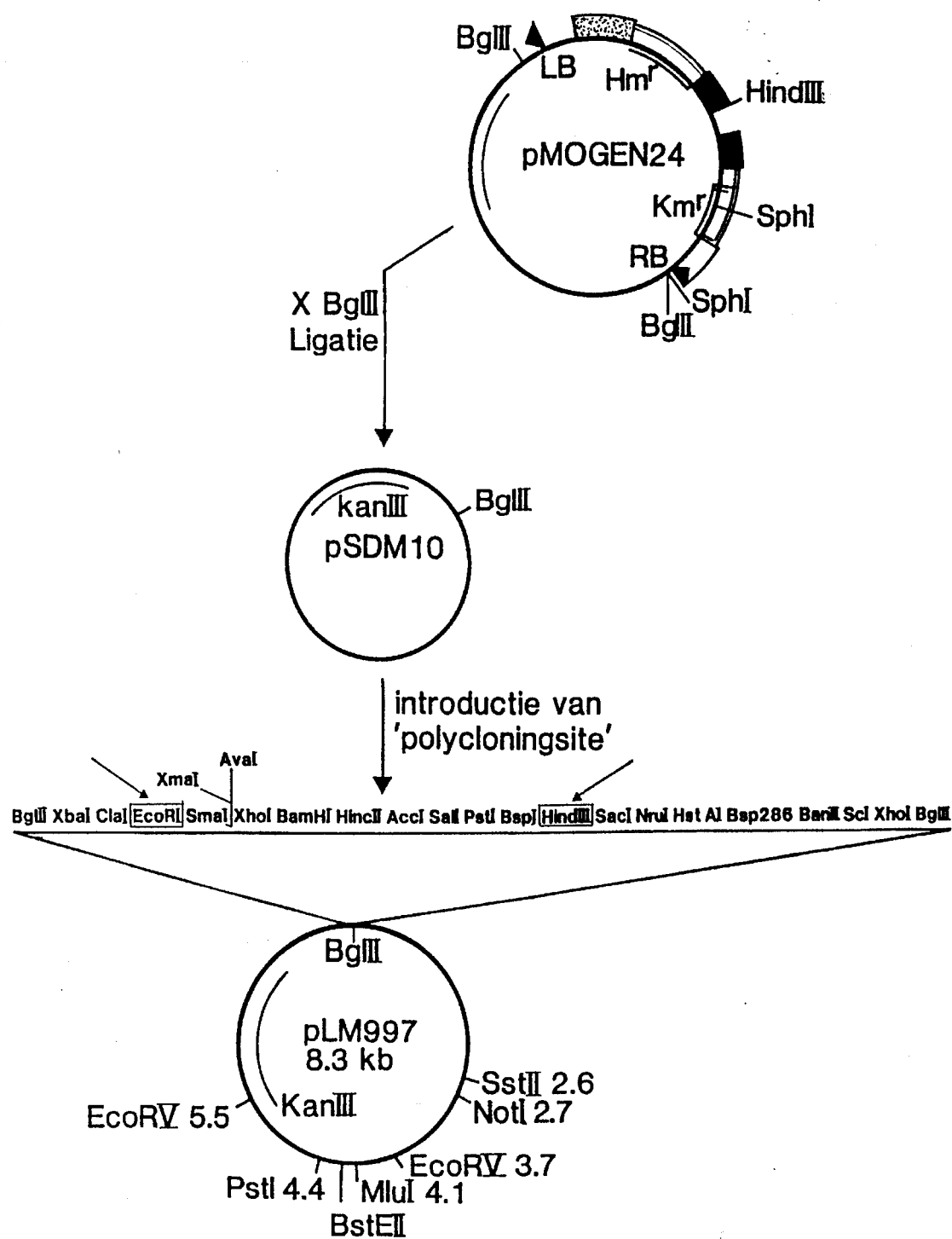
FIG. 7 shows the construction of plasmid pLM997.

FIG. 5:

Construction of the 3' deletion mutants of the Km$^r$ gene starting from the plasmid pSDM4. A 75 bp HindIII/BamHI fragment with synthetic octopine type left border sequences was introduced behind the intact Km$^r$ gene on pSDM4, resulting in pSDM8. The sequence of the fragment containing the synthetic left border is shown in FIG. 6. Through deletion of an EcoRV/BamHI- or an EcoRV/RsrII-fragment, respectively the plasmids pSDM8* and 3'▲IIa were obtained. In this way the intact or defective Km$^r$ gene is located between border sequences. In pSDM9 the 110 basepair HindIII/BglII fragment of the plasmid pRAL3912 (Hoekema et al., 1985) was placed behind the Km$^r$-gene. This fragment contains the wildtype octopine left border sequence. The plasmids pSDM9* and 3'▲IIb were obtained from pSDM9 by deleting the AccI/BstEII fragment or the AccI/RsrII fragment, respectively. The T-regions of the plasmids pSDM8*, pSDM9*, 3'▲IIa and 3'▲IIb were transferred as EcoRI/HindIII fragment to the binary vector pLM997 (see FIG. 7), resulting in the vetors pSDM200, pSDM210, pSDM201 and pSDM211.

FIG. 6:

The sequence of the synthetic HindIII/BamHI fragment on which the left T-DNA border of the octopine type is located. The recognition sites for different restriction enzymes are indicated above and beneath the sequence.

FIG. 7:

Construction of plasmid pLM997. Plasmid pLM997 was derived from pMOGEN24 by deletion of the BglII fragment carrying the T-DNA followed by the introducion of a so-called polycloningsite (a synthetic DNA-fragment containing several recognition sites for restriction enzymes) in the remaining BglII restriction site. The EcoRI and HindIII sites in which the EcoRI/HindIII fragments of plasmids pSDM8*, pSDM9*, 3'▲IIa and 3'▲IIb were inserted, are indicated with arrows.

FIG. 8:

Illustration of the detection of recombination events via Southern analysis and the polymerase chain reaction (PCR). Genomic DNA of Km$^r$ plant lines obtained from the cotransformation experiments was digested with EcoRI/BclI and HindIII. The fragments that were detected after blotting and hybridization with the 3'OCS- or the NPTII-probe are depicted. A 2.1 Kb fragment is indicative for the presence of a repaired NPTII gene. Digestion with HindIII only generates junction fragments (i.e. fragments that contain the junction between plant DNA and the integrated T-DNA copy). The number of HindIII fragments was used as an indication for the number of T-DNA inserts in the plant genome.

PCR analysis using primers 2 and 3 was performed on plants in which the 2.1 Kb EcoRI/BclI fragment was not detected. The primers anneal within the regions that are deleted in the defective NPTII genes. Only when a repaired NPTII gene is present a 593 bp fragment is amplified. Primers 2 and 3 are indicated in the figure by arrows that point from the 5'- to 3'-end.

sLB=synthetic left T-DNA border repeat; B=BclI; E=EcoRI; H=HindIII.

FIG. 9:

Detection of recombinants after Agrobacterium mediated transformation of protoplasts of the target line with the T-DNA construct of pSDM101 using the polymerase chain reaction (PCR). The target locus of the plant line 104(.1.6) is depicted as are the T-DNA constructs of pSDM100 and pSDM101. The 20 basepair long oligonucleotides 1 and 2 that were used in the PCR, are indicated with arrows that point from the 5'- to the 3'-end.

FIG. 10:

The translational SSU-NPTII fusion constructs (see example 9 and 11). The constructs were cloned as HindIII or PstI/HindIII fragment into the poly-cloning sites of pIC20R, resulting in the plasmids pNTSS1, pNTSS2, pNTSS3 and pNTSS4. pNTSS1 contains the fusion gene that consists of the complete sequence of the SSU clone (HindIII fragment) and has the 1690 bp BamHI NPTII module from pSDM53 inserted in the 4th. exon. The coding sequences of the SSU gene (exons) are indicated with the boxes numbered 1 to 4. Non-coding regions of the gene such as promoter, introns and terminator are indicated by a single line. Construct pNTSS2 was derived from pNTSS1 and lacks the promoter and part of the coding region up to the PstI site (P1). Plasmid pNTSS3 contains the complete SSU clone that has the BglII/BamHI NPTII module inserted in the 2nd.exon. pNTSS4 contains the promoterless fusion gene of pNTSS3. Below the constructs the length of the fusion genes is indicated in basepairs. From the pIC plasmid the fusion constructs were excised as SalI/XhoI fragment and cloned in the SalI/XhoI sites between the borders of the binary vector pSDM14, resulting in pNTSS11A/B, pNTSS12A/B, pNTSS21A/B and pNTSS22A/B. A/B indicates the orientation of the fragment in pSDM14. Only the B orientation is shown here. The construction of pSDM14 is depicted in FIG. 11. O.D.=overdrive sequence.

Restriction sites: B1=BamHI, B2=BglII, E1=EcoRI, H1=HpaI, H3=HindIII, K1=KpnI, P1=PstI, S1=SalI, X1=XhoI.

FIG. 11

The EcoRI/XmaIII fragment that was used to construct pSDM53 was composed of 2 complementary oligonucleotides (I and II). The sequence of the fragment is shown and restriction sites are indicated above the sequence. Below the sequence the amino acids of the translation product are given. The numbers 2 and 3 below the amino acids refer to the second and third codon of the NPTII coding sequence. At the bottom of the figure the DNA and amino acid sequence of the fusions between the coding regions of SSU and NPTII are shown.

FIG. 12:

The construction of the binary vector pSDM14. See example 10 for detailed description. See also the legend.

FIG. 13:

Plasmid pNTSS512 contains an alternative T-DNA construct to target the SSU locus in tobacco cells. The construction of this plasmid is described in example 12. The boxes 3' and 5'indicate the downstream and upstream non-coding sequences of the aux-2 gene. The non-coding sequences of the SSU-gene are indicated by a line and the coding regions (exons) are depicted by the boxes 1 to 4. See also the legend.

Restriction sites: B1=BamHI, B2=BglII, E1=EcoRI, H1=HpaI, H3=HindIII, K1=KpnI, P1=PstI, S1=SalI, X1=XhoI.

FIG. 14A–B:

A consensus for T-DNA replacement and insertion constructs that can be used to achieve gene targeting. See chapter "detailed description" for explanation of the numbered boxes.

The following Examples only serve to illustrate the invention and do not mean to limit the scope of its applications.

EXAMPLE 1

Transformation of tobacco protoplasts by cocultivation with *Agrobacterium tumefaciens*

Cocultivation is the plant cell transformation method in which plant protoplasts and Agrobacterium are incubated together and where during subsequent regeneration from protoplast to callus selection takes place on the transfer of T-DNA (Marton et al., 1979; Fraley et al., 1984).

For the experiments described below the following protocol for cocultivation of tobacco protoplasts with *A. tumefaciens* was used. *Nicotiana tabacum* cv. petit havana SR1 plants were axenically grown in Magenta boxes, filled with 50–60 ml Daichin-agar (0.6%) solidified MS30-medium (Murashige and Skoog, 1962; contains 30 g sucrose/l). Every 5–8 weeks apical meristems of the plants were transferred to fresh medium. Protoplasts were prepared from leaves of 5–8 week old axenically grown tobacco plants by overnight incubation at 26° C. in K3 0.4M sucrose medium (Nagy and Maliga, 1976), 1% cellulase R10, 0.1% Macerozyme R10 and 0.1% MES. The protoplasts were washed one time in K3 sucrose medium, diluted to $1\times10^5$ cells/ml in K3 medium containing 0.4M glucose ($K_3G$) and distributed in batches of 7 ml in 9 cm petridishes. They were incubated overnight in the dark prior to cocultivation with the bacteria. Agrobacterium strains were grown at 29° C. in LB medium containing 20 mg/l rifampicin and 50 mg/l kanamycin. End log phase cultures were diluted in $K_3G$ medium and the bacteria were added to the protoplasts at a ratio of approximately 100 bacteria per protoplast. After three days of cocultivation the protoplasts were embedded in agarose discs by mixing 5 ml protoplasts with 5 ml 0.8% low melting-type agarose (Sigma) in SII medium (Muller et al., 1983) containing 0.1M sucrose and 0.2M mannitol. The bacterial growth was stopped by the addition of cefotaxim and vancomycin to final concentrations of 200 mg/l and 100 mg/l, respectively. After 10 days 15 ml SII medium containing either 50 mg/l kanamycin or 10 mg/l hygromycin was added to the discs. Seven days later 15 ml SII medium with kanamycin at 100 mg/l and hygromycin at 20 mg/l was added. From this moment on the medium was refreshed weekly by replacing 15 ml old medium with 15 ml fresh SIII medium (100 –150 mg/l kanamycin, 20–30 mg/l hygromycin). This medium is identical to the SII-medium except for the mannitol concentration which is 0.1M instead of 0.2M. The plating efficiency was determined by incubation of ⅛ part of an agarose disc on liquid medium without selection. The hormone regime in the K3 and SII media was 1 mg/l NAA, 0.2 mg/l BAP and 0.1 mg/l 2.4D. In the SIII medium 2.4D was omitted. Cefotaxim and vancomycin were added to final concentrations of 200 mg/l and 100 mg/l, respectively.

Microcalli were harvested from selective or non selective medium 4 to 5 weeks after embedding the protoplasts and were transferred to MS30 medium (Murashige and Skoog, 1962) containing 3% sucrose, 1.0 mg/l NAA and 0.2 mg/l BAP and solidified with 0.6% agar (Daichin). Shoots were induced on solid MS15 medium containing 1.5% sucrose, 1.0 mg/l BAP and 0.1 mg/l NAA. Solid medium also contained 100 mg/l cefotaxim and 50 mg/l vancomycin and for selection 100 mg/l kanamycin or 20 mg/l hygromycin was added. Shoots were tested for $Km^r$ or $Hm^r$ by allowing them to root on MS15-medium to which 20mg/l hygro. or 100mg/l kana. was added.

EXAMPLE 2

Construction of defective NPTII genes

Construction of the vectors containing different defective NPTII genes started from the binary vector pMOGEN24 (see FIG. 1). This plasmid was derived from the vector pROK1 (Baulcome et al., 1986) and contains between the borders of the nopaline Ti- plasmid pTiT37 the genes, functional in plants, for kanamycin resistance ($Km^r$) and hygromycin resistance ($Hm^r$) in opposite orientation. The vector pMOGEN24 is obtained through standard recombinant DNA techniques (Maniatis et al., 1982) from pROK1 by cloning the coding region of the *E. coli* hygromycin phosphotransferase (Hpt) gene (Gritz et al., 1983) as a BamHI-fragment in the BamHI restriction site in pROK1.

Consequently, the coding sequence of the HPT gene, from 19 basepairs in front of the translation initiation codon up to 20 basepairs behind the translationstop codon becomes located between the 35S CamV promoter and the transcription terminator of the nopaline synthase gene.

Just in front of the actual translation startcodon (ATG) another ATG codon is present. Because this first codon might disturb translation from the actual codon the sequence of this codon was changed into ATA via oligonucleotide mutagenesis, a standard recombinant DNA technique. Accordingly, the BamHI sites on both sides of the HPT fragment was deleted by filling in using Klenow polymerase (Maniatis et al., 1982).

The BglII/HindIII fragment from pMOGEN24 with on it the right border and the Km$^r$ gene was transferred to the plasmid pUC12 (Messing, 1983; see FIG. 1) after it had been digested with BamHI and HindIII (Maniatis et al., 1982). Subsequently, the transcription termination signal of the nopaline synthase gene was replaced by the termintion signal of the octopine synthase gene. This resulted in the plasmid pSDM2 (FIG. 1) on which are located succesively: 1) the right border of pTiT37 (RB), 2) the promoter region of the nopaline synthase gene up to the base in front of the ATG start codon (5'NOS, Bevan et al., 1983), 3) the coding region of the NPTII gene derived from Tn5 from the SauIIIa site ±10 basepairs (bp) in front of the ATG start codon till the PstI site that is located ±370 bp behind the TGA stop codon (Beck et al., 1982) and 4) a 700 bp PvuII fragment that contains the transcription termination signal of the octopine synthase gene (3' OCS, Gielen et al., 1984).

To simplify reintroduction of the Km$^r$ gene of pSDM2 or defective mutants derived therefrom into the binary vector, a XhoI-linker was introduced at the EcoRI-site (FIG. 1). This results in plasmid pSDM4. A XhoI-site was introduced in the binary vector pMOGEN24 as well, by replacing a SphI fragment with a XhoI-linker. SphI cuts in pMOGEN24 just before the right border and within the coding region of the Km$^r$ gene. Thus, plasmid pSDM5 was obtained (FIG. 3).

Finally, to be able to isolate the T-DNA constructs integrated in the plant genome by recombination via a Lambda vector library (Maniatis et al., 1982), the so-called supF gene located on a EcoRI fragment derived from plasmid πVX (Seed, 1983) was cloned next to the Km$^r$ gene. Using the so-called amber/suppressor system, also used and described by Smithies et al., (1985), the Lambda phage library can be enriched for the fragments that contain this supF gene. The EcoRI restriction sites of the supF fragment were filled in with Klenow polymerase and ligation of BamHI-linkers to the fragment was followed by digestion with BamHI. The BamHI fragment was ligated into the BamHI site of pSDM4, resulting in plasmid pSDM7 (FIG. 1).

Figure 4:
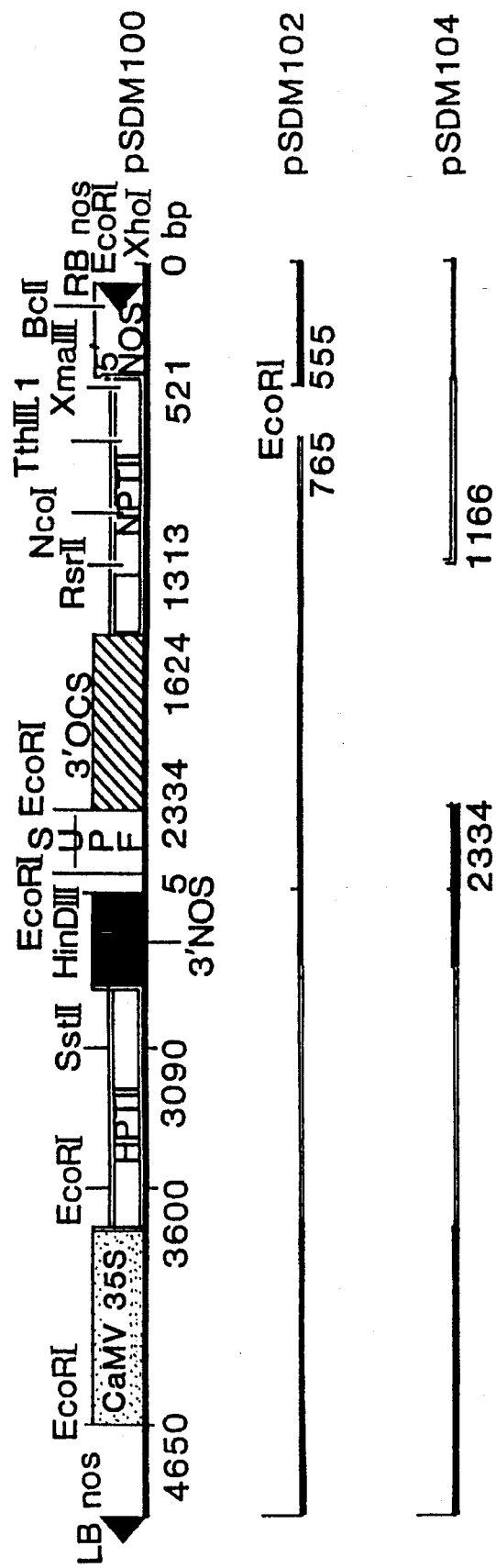
FIG. 4 shows an overview of the T-region of plasmid pSDM100.
Figure 8:
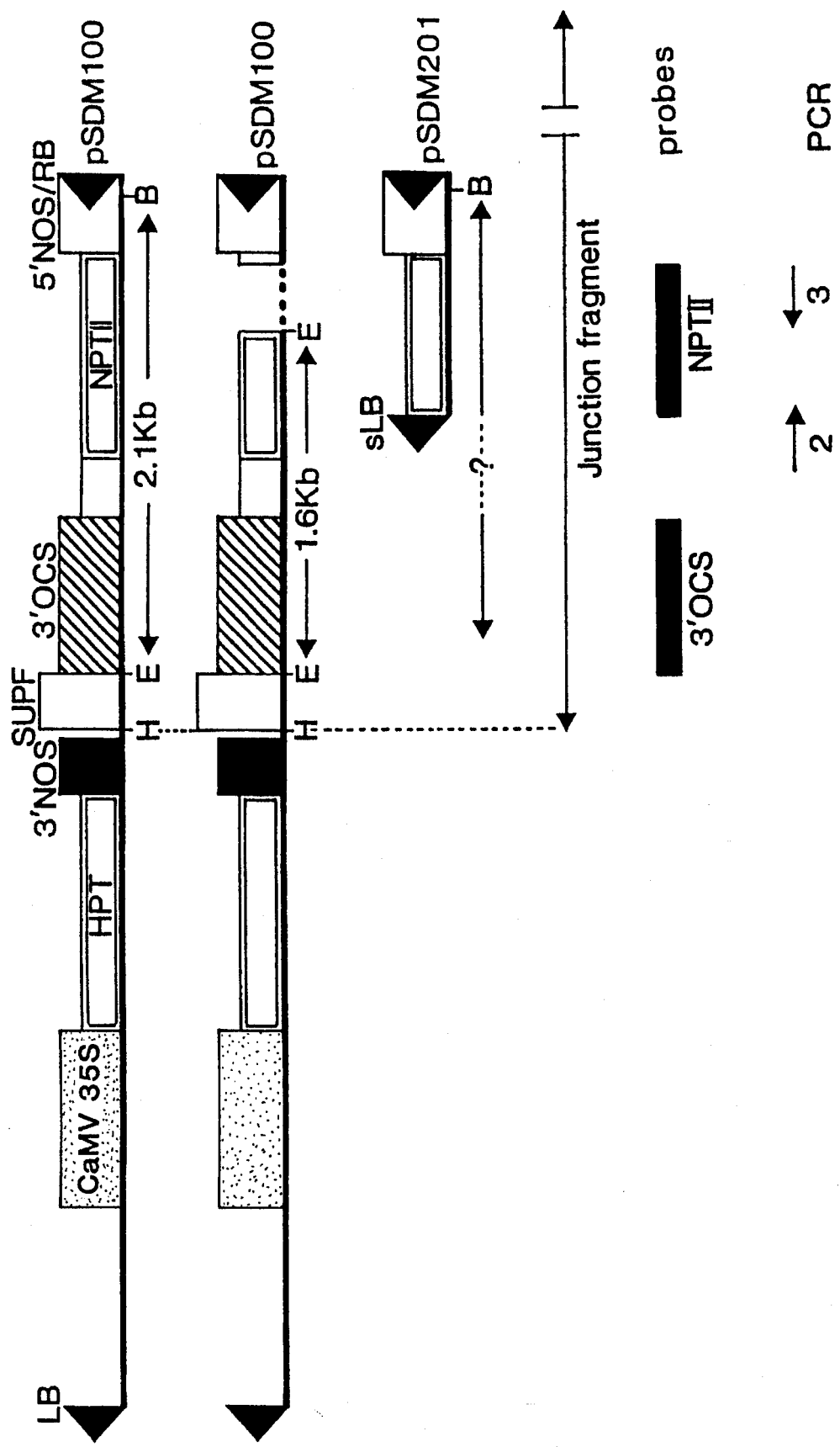
FIG. 8 shows the detection of recombination events via Southern analysis and the polymerase chain reaction.

The defective Km$^r$ genes were derived from pSDM7 (see FIG. 2). As an illustration the construction of one of the defective genes, namely the 5'▲II construct, is extensively described below. The construction of other defective Km$^r$ genes is roughly indicated in FIG. 2. For the construction of 5'▲II, pSDM7 was cut with restriction enzymes TthIII.1 and XmaIII, the ends were made blunt by filling in with Klenow polymerase and on the site of deletion an EcoRI-linker (10 bp) was inserted. Due to this modification a sequence that codes for an active region of the NPTII enzyme was deleted (Beck et al., 1982). The sequence at the site of the mutation was checked using the dideoxy-sequencing method (Sanger et al., 1977). Like the other defective Km$^r$ genes 5'▲II was cloned as a XhoI/HindIII fragment into the vector pSDM5 that had been cut beforehand with XhoI and HindIII. The resulting plasmid was called pSDM102 (FIG. 3, 4 and 8). The 3'▲ mutants used in the experiment described in Example 3 are depicted in FIG. 5. Starting from the intact Km$^r$ gene located on plasmid pSDM4, two types of constructs were made. One type was obtained by introducing a 75 bp HindIII/BamHI fragment containing the synthetic octopine left border sequence (FIG. 6) behind the intact Km$^r$ gene on pSDM4. This resulted in plasmid pSDM8. Through deletion of a EcoRV/BamHI- or a EcoRV/RsrII-fragment respectively the plasmids pSDM8* and 3'▲IIa were obtained. The defective gene (3'▲IIa) lacks part of the coding region of the NPTII gene and the transcription termination signal. For the other construct type a HindIII/BglII fragment, containing the wildtype octopine left border sequence derived from the plasmid pRAL3912 (Hoekema et al., 1985) was transferred to pSDM4 that had been digested with HindIII and BamI. From the obtained plasmid pSDM9 the AccI/RsrII fragment on which part of the coding region of the NPTII gene, the transcription termination signal (3'OCS) and a part of the HindIII/BglII fragment from pRAL3912 is located, is deleted. This results in 3'▲IIb. An intact Km$^r$ gene with the same border fragment behind the 3'OCS was obtained by deleting the AccI/BstEII fragment (pSDM9*). The restriction site for BstEII is located behind the transcription termination signal at the end of the 3'OCS part. The constructs with an intact or defective Km$^r$ gene between the right and left border (respectively pSDM8*, pSDM9*, 3'▲IIa and 3'▲IIb) were transferred as EcoRI/HindIII fragment to plasmid pLM997 (see FIG. 7), that was cut beforehand with EcoRI and HindIII. This resulted in the binary vectors pSDM200, pSDM210, pSDM201 and pSDM211, respectively Binary plasmids were mobilized by a triparental mating (Ditta et al., 1980) to a rifampicin resistant (rif$^r$) Agrobacterium strain, that already contained a helper Ti-plasmid without T-DNA (e.g. Hoekema et al., 1983; Deblaere et al., 1985). Conjugants were selected on LB agar medium (Maniatis et al., 1989) containing 20 mg/l rifampicin and 50 mg/l kanamycin. Agrobacterium strains were named after the binary plasmid they contain.

EXAMPLE 3

Homologous recombination in tobacco protoplasts between two simultaneously introduced T-DNA's The possibility of homologous recombination between two T-DNAs in a plant cell was tested by transforming tobacco protoplasts with two T-DNAs, by simultaneously cocultivating the tobacco protoplasts with two different Agrobacterium strains. Both strains were derived from the same non-oncogenic helper strain, but harbour a different binary vector. The T-DNA of each binary vector contained a different defective NPTII gene, one with a deletion in the 5'part of the coding region of the gene (pSDM102, FIG. 4 and 8) and the other with a deletion in the 3' part of the gene (pSDM201, FIG. 5 and 8). In example 2 the construction of the different defective NPTII genes is described in extenso.

Tobacco protoplasts were cocultivated according to the procedure described in example 1, with the following strains: 1) 1,5×10$^6$ protoplasts with SDM102 alone as a negative control, 2) 1,5×10$^6$ protoplasts with SDM201 alone or SDM211 alone as a negative control, and 3) 1,5×10$^6$ protoplasts with both SDM102 and SDM201 or both SDM102 and SDM211.

(Co-)transformation frequencies of the various constructs were determined in a smaller experiment. Here, 5×10⁵ protoplasts were cocultivated with both SDM102 and SDM200 or both SDM102 and SDM210. For strain SDM102 the transformation frequency was determined by using the hygromycin resistance gene present on the T-DNA of plasmid pSDM102. Strains SDM200 and SDM210 were used to estimate the frequency with which the T-DNA of respectively strains SDM201 and SDM211 was transferred to tobacco cells. The T-DNA of the binary vector of strain SDM200/SDM210 is similar to that of SDM201/SDM211 except that it contains an intact NPTII gene construct between right- and left T-DNA border instead of the 3' deleted gene. Approximately 5–7% of the protoplasts regenerated to callus. Of these surviving calli ±20% appeared to be transformed with the 102 construct, whereas for both the construct 200 (=201) and the construct 210 (=211) transformation percentages were observed of ±15%. Of the calli that had already been transformed with one construct (Hm$^r$ or Km$^r$) approximately 30% appears to be transformed with the other construct (Hm$^r$ or Km$^r$). In the cocultivation experiment where protoplasts were co-transformed with a 5'▲-construct (102) and a 3+▲-construct (201 or 211) restoration was found in 1–4% of the co-transformed calli. In the negative controls only one Km$^r$ calli was obtained. This callus did not contain a repaired Km$^r$ gene and progeny of this callus did no longer show kanamycine resistance. A clear difference in transformation frequency between the 201 construct (3'▲ with synth. LB) or the 211 construct (3'▲ with wildtype LB) was not observed.

The obtained Km$^r$ calli were regenerated into plants as described in example 1. In leaf extracts from these plants NPTII activity could be detected, using non-denaturing gels (Platt and Yang, 1987), at the correct position in the gel. The plants were also analysed on the DNA level. Accordingly, proof for the presence of a restored Km$^r$ could be provided.

Theoretically, the NPTII gene could have been restored via homologous recombination in the bacterial background. This could only be possible if transfer of the binary vectors between the two bacterial strains should occur. Crossing experiments described in the following example (4) excluded this possibility.

EXAMPLE 4

The control crossing-experiment

To test whether transfer of binary vectors occured between Agrobacterium strains, a donor- and a recipient-strain were coincubated for 3 days at 28° C. A total of 10⁹ bacteria of each strain was mixed and spotted on a nitrocellulose filter lying on either solid LB medium or on a layer of tobacco suspension cells that had been plated on solid MS30 medium containing 0.5 mg/l of the plant hormone 2,4D. In addition similar coincubations were performed in the presence of E. coli helper strain RK2013 which is used in triparental matings (Ditta et al., 1980). The donor strain SDM201 is rif$^r$ and contains the binary vector pSDM201 that carries a bacterial gene for kanamycin resistance (Km$^r$). The recipient strain LBA285 is a spontaneous spectinomycin resistant (spc$^r$) derivative of strain LBA202 and does not contain any plasmid. LBA285 behaves like a wildtype recipient for Ti-plasmids in conjugation experiments. (Hooykaas et al., 1980). If transfer of the binary vector pSDM201 should occur from SDM201 to LBA285, spc$^r$Km$^r$ colonies would be found on selective plates. The bacteria were plated on LB medium containing 250 mg/l spectinomycin and 50 mg/l kanamycin after coincubation. Resistant colonies were found at a low frequency (0.8×10$^{-8}$). These were not genuine transconjugants, because they were all rif$^r$. Indeed, incubation of strain SDM201 alone gave rise to spc$^r$rif$^r$Km$^r$ colonies at a comparable frequency. From this we concluded that these colonies represent spontaneous spc$^r$ derivatives of strain SDM201. Transfer of the binary vector did occur when the donor and recipient strain were coincubated together with E. coli helper strain RK2013 (Ditta et al., 1980). This confirmed that genes essential for efficient transfer of binary vectors are not present in the strains used in our transformation experiments but have to be provided in trans to obtain conjugation. When E. coli strain RK2013 was provided as helper, the frequency of transfer after coincubation on MS medium in the presence of plant cells (8×10$^{-7}$/recipient) was even lower than when coincubation was performed on bacterial (LB) medium (1×10$^{-3}$/recipient).

Consequently, we can conclude that homologous recombination between the T-DNAs had indeed taken place after co-introduction in the plant cell.

EXAMPLE 5

Southern blot analysis of plants derived from Km$^r$-calli

Plant DNA was isolated from not fully expanded leaves of plants in the growth room as described (Mettler, 1987) and purified on a CsCl-gradient. The concentration of the obtained DNA suspension was determined by measuring the OD$_{260}$. Approximately 10 μg of genomic DNA was used for digestion with restriction enzymes. Following separation on a 0.7% agarose TBE gel (Maniatis et al., 1989) the DNA was transferred to a Hybond N membrane (Amersham; Cat. No. RPN.303N ) by capillary blotting and the membrane was (pre-)hybridized according to the Hybond N protocol. Final washing was performed in 0.3× SSC, 0.1% SDS at 65° C. DNA probes labelled with [α$^{32}$P]-dCTP (specific activity: 0.5–1×10⁹ dpm/μg DNA) were obtained using the mixed primer method (Boehringer Mannheim kit; Cat. No. 10044 760). The chromosomal DNA isolated from plants regerated from kanamycin resistant calli was analysedaccording to the method described above.

Chromosomal DNA isolated from 2 transgenic plants each containing a single copy of the 102 construct, from a plant containing the 100 construct and from a non-transformed N. tabacum cv. petit havana SR1 were used for reconstruction.

In FIG. 8 is depicted which internal bands are to be expected after digestion with EcoRI and BclI. The 5'deletion construct (102) gives an internal band of 1.6 kilobasepairs (Kb), while the intact (correctly repaired) Km$^r$ gene should give a band of 2.1 Kb. Digestion with HindIII only generates so-called junction fragments. When the probe only comprised the 3'part of the Km$^r$ gene (e.g. the 0.7 Kb PvuII fragment with the 3'OCS, Gielen et al., 1983) integrated copies of the 3'deletion mutant were not observed on the blot, which simplified the interpretation.

The expected 2.1 Kb fragment, corresponding with a repaired NPTII gene, was present in almost all Km$^r$ plants tested (FIG. 8). In case the 2.1 Kb fragment could not be detected the presence of a repaired gene could be shown by PCR-analysis using primers 2 and 3 (FIG. 8).

EXAMPLE 6

Construction of transgenic tobacco plants containing a defective NPTII gene as target-locus for homologous recombination Transgenic tobacco plants were obtained by co-cultivating leaf discs of axenically grown tobacco plants (Horsch et al., 1985) with bacterial strain SDM104. After cocultivation, the leaf discs were placed on solid MS30-medium with callus inducing hormones (1.0 mg/l NAA and 0.2 mg/l BAP) and the antibiotics cefotaxim (200 mg/l) and vancomycin (100 mg/l). After one week the leaf discs were transferred to callus-inducing medium with 20 mg/l hygromycin. Resistant calli were cut and transferred to shoot-inducing medium (MS15, 1 mg/l BAP, 0.1 mg/l NAA, 100 mg/l cefotaxim and 50 mg/l vancomycin). Shoots were cut and tested for Hm$^r$ by allowing them to root on hormoneless MS30-medium with 20 mg/l hygromycin.

Figure 9:
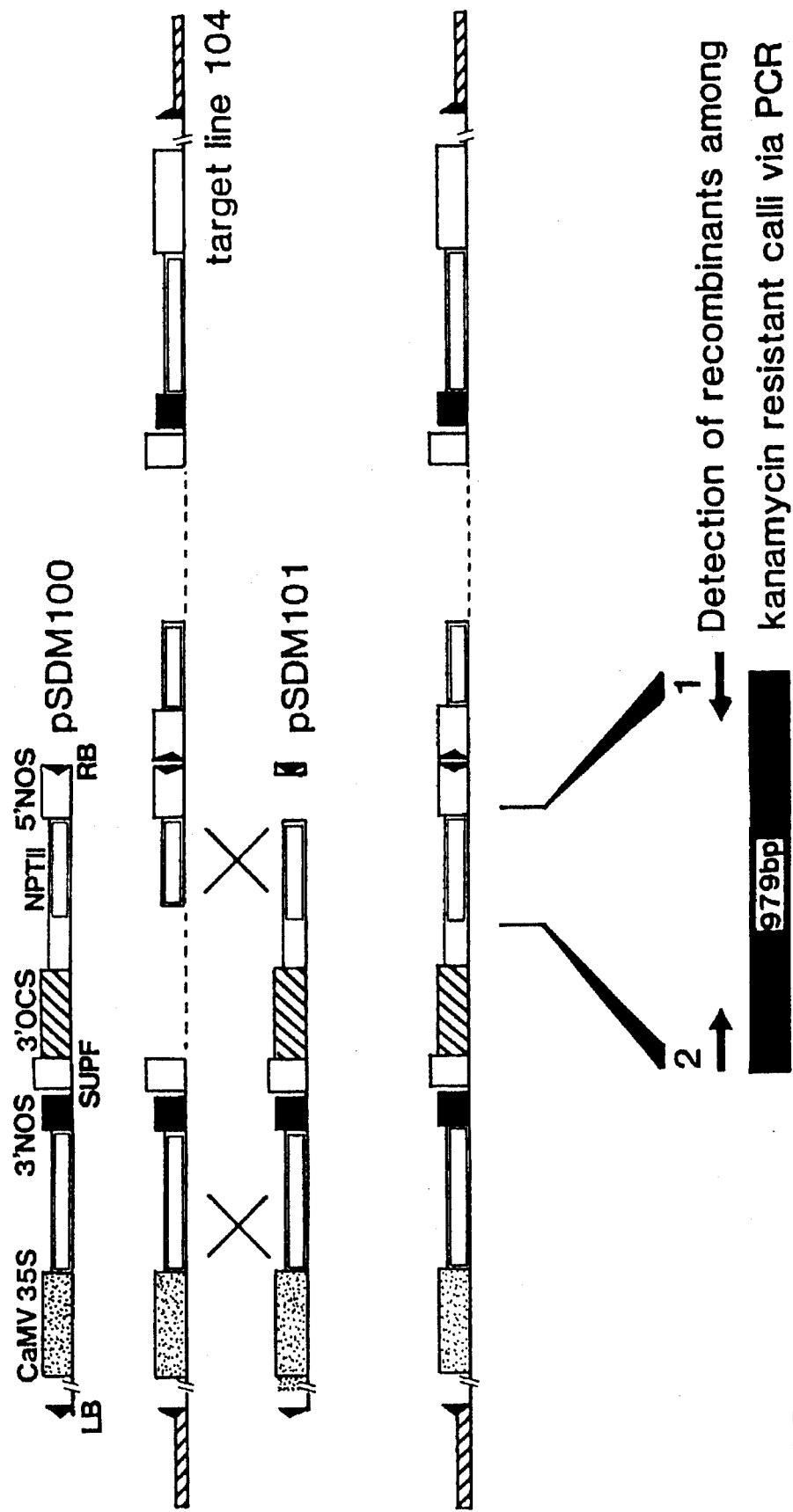
FIG. 9 shows the detection of recombinants after Agrobacterium mediated transformation of protoplasts.

The transgenic plants obtained with the method described above were analysed at the DNA level (see example 5). Subsequently, plant lines were selected that showed a simple T-DNA integration pattern. Plant line 104(.1.6) transformed with the 104-construct was used as acceptor plant for the targeting experiments. This line appeared to have 2 T-DNA copies integrated in inverted orientation at the same position in the plant genome (FIG. 9).

EXAMPLE 7

Restoration of a defective NPTII gene in a transgenic tobacco plant via homologous recombination using Agrobacterium-mediated DNA-transfer Protoplasts of transgenic plant 104.1.6 were co-cultivated with Agrobacterium strain SDM101. Cocultivations were carried out with approximately $2 \times 10^7$ protoplasts. To determine the transformation frequency $1 \times 10^6$ protoplasts were cocultivated with Agrobacterium strain SDM100. The cocultivation experiments were carried out according to the procedure described in example 1. In two independent experiments, protoplasts of plant line 104 were cocultivated with an Agrobacterium strain harbouring the binary vector pSDM101. The plasmid pSDM101 contains a NPTII gene with a 5'deletion, next to the hygromycin resistance marker (FIG. 9). The transformation experiments resulted in 285 and 281 kanamycin resistant calli, respectively. In most of these calli gene targeting had not occurred. Results which are not shown here suggested that the 5'deleted NPTII gene at the repair T-DNA had been fused to an endogenous plant gene.

In recent articles on homologous recombination in animal cells the polymerase chain reaction (PCR) technique is used for quick detection of a homologous recombination event (Kim & Smithies, 1988; Zimmer and Gruss, 1989). Also in our experiments we used the PCR method to screen for kanamycin resistant calli in which an intact NPTII gene had been formed via homologous recombination (FIG. 9). A PCR with two primers that anneal within the regions deleted in either the target NPTII gene or the repair construct should result in amplification (of a 979 bp size fragment) only if an intact NPTII gene is present. In this way a total number of 213 calli was screened. Three calli appeared to be PCR-positive and plants were regenerated from these calli resulting in plant lines 1, 2 and 3, respectively.

EXAMPLE 8

Molecular analysis to detect targeting events

The chromosomal DNA of the plant lines was analysed using the Southern blot method described in example 5. DNA was cut with the restriction enzymes EcoRI/BclI and HindIII, the fragments were separated on gel and subsequently transferred to Hybond-N membrane. Hybridisation was performed with an internal NPTII probe (the 610 bp XmaIII/RsrII fragment, see FIG. 8).

In plant line 1, one of the 3' deletion mutant copies of the NPTII gene present on the target locus had been restored by the incoming T-DNA via homologous recombination. Wild-type NPTII activity could be detected in leaves of this plant line (Platt and Yang, 1987), thereby confirming the presence of an intact NPTII gene.

EXAMPLE 9

Construction of the SSU-fusion genes

In order to isolate an active member of the SSU multigene family a subgenomic library of *N. tabacum* SR1 was constructed in lambda phage PDJII (Maniatis et al., 1982). Using a probe specific for a SSU cDNA-clone of *N. tabacum* cv. petit havana SR1, a clone containing a SSU-gene with 3 introns (Mazur et al., 1985) was isolated from this library. The active gene is located on a 2.4 Kb basepair HindIII fragment. Both the restriction map and the DNA-sequence of the clones isolated by us corresponded with the published data (Mazur et al., 1985). The HindIII fragment was cloned in pIC19H (Marsh et al., 1984) resulting in plasmid pSIC1. This gene was used for the construction of chimaeric SSU-NPTII genes (FIG. 10). To do this a NPTII insertion module was constructed (clone pSDM53) by:

a) replacing the EcoRI/XmaIII fragment of pSDM4 (see FIG. 1) containing the nopaline synthase promoter and the start of the coding region by a 51 basepair synthetic EcoRI/XmaIII fragment (see FIG. 11B) on which a unique BamHI and a unique BglII restriction site are located.

b) removing both PstI restriction sites from the NPTII-sequence (Beck et al., 1982). The PstI site in the coding region was removed by changing a G into an A on position 1733 in the Tn5 sequence (Beck et al., 1982), using M13/oligonucleotide mutagenesis (mutagenesis kit from Biorad). Consequently, no changes were introduced in the amino acid sequence of the NPTII protein. The other PstI site is located outside the coding region and was removed by cutting with PstI, blunt-ending with Klenow in the presence of dCTP, subsequently cutting with SmaI and closing by ligation. Due to this the fragment ranging from base 2519 till base 2656 in the Tn5 sequence (Beck et al., 1982) of the 3' non-coding region was deleted.

For the construction of one fusion gene the 1,7 Kb BamHI fragment of the promoterless NPTII and the 3' OCS terminator was inserted into a BamHI site of the rbcS-gene on pSIC1. The resulting plasmid pNS1 contains a translational fusion between the rbcS and the NPTII in the fourth exon of the rbsS gene.

For the construction of the other SSU-NPTII fusion in the second exon, in pSIC1 the BamHI site was removed from the fourth exon by filling in with Klenow-polymerase This resulted in plasmid pSIC2. Subsequently, in the second exon of pSIC2 a new BamHI site was introduced using M13/ oligonucleotide mutagenesis (mutagenesis kit of Biorad). Due to this a G was changed into a T and an A into a C, respectively on positions 1383 and 1385 in the sequence of Mazur et al., (1984). In the resulting plasmid pSIC3, the 1,7 Kb BglII/BamHI fragment from pSDM53 was cloned into the new BamHI restriction-site. The clone pNS2 thus obtained contains a translational fusion between the rbcS and the NPTII in the second exon of the rbcS-gene.

EXAMPLE 10

Construction of the binary vector pSDM14

The plasmid pSDM10 (see FIG. 7) served as a basis for the construction of the binary vector pSDM14. Synthetic borders and a fragment containing the overdrive sequences were transferred to pSDM10 by the following method. The overdrive sequence of pTiAch5 is located on a BclI/SacI fragment (14087-14710, Barker et al., 1983). This fragment was cloned in pIC20R (Marsh et al., 1984) cut with SacI and BamHI. From pIC20R, the 'overdrive' was cloned as a SacI/EcoRI fragment to pUC19 (xSacIxEcoRI). The resulting plasmid was digested with SacI and KpnI and a synthetic KpnI/SacI fragment containing the right T-DNA border was ligated into it. By cutting the resulting plasmid with HindIII and KpnI a HindIII/KpnI fragment containing the left T-DNA border could be cloned. From this plasmid pBINSB2 the EcoRI/HindIII fragment was excised. The ends of the fragment were filled in with Klenow-polymerase, BglII-linkers were ligated to it, and following digestion with BglII the fragment was ligated in pSDM10. In this way pSDM14 was obtained.

EXAMPLE 11

Cloning of the rbcS-NPTII fusion genes in pSDM14

From pNS1 and pNS2 the HindIII fragments with the intact fusion genes and the PstI/HindIII fragments with the promoterless rbcS-NPTII fusions were cloned into pIC20R (Marsh et al., 1984), resulting in plasmids pNTSS1, 2, 3, and 4 respectively (see FIG. 10). From there, the fusion genes were ligated as SalI/XhoI fragments in the binary vector pSDM14 (FIG. 11) that had been cut with SalI/XhoI.

The resulting plasmids pNTSS11 (A/B), pNTSS12 (A/B), pNTSS21 (A/B), and pNTSS22 (A/B) contain between a synthetic right and left border of the octopine Ti-plasmid, the intact 4th. exon fusion gene, the promoterless 4th. exon fusion gene, the intact 2nd. exon fusion gene, and the promoterless 2nd exon fusion gene, respectively. A and B refer to the orientation of the XhoI/SalI fragment in pIC20R. In FIG. 10 only the B orientation is depicted. The binary plasmids were crossed to a Agrobacterium helper strain that contains the Vir-region on a helper Ti-plasmid (example 2), resulting accordingly in strains NTSS11, NTSS12, NTSS21, and NTSS22.

EXAMPLE 12

Site-directed mutagenesis of one of the rbcS-genes via cocultivation of the protoplasts of *Nicotiana tabacum* cv. petit havana SR1 with Agrobacterium In separate transformation experiments $10^7$ tobacco protoplasts were co-cultivated with the Agrobacterium strain NTSS12 and with the strain NTSS22. These strains respectively contain the promoterless 4th exon rbcS-NPTII fusion gene and the promoterless 2nd. exon rbcS-NPTII fusion gene between the borders of the T-DNA residing on the binary vector. As positive controls the strains NTSS11 and NTSS21 were co-cultivated with $10^6$ tobacco protoplasts. The cocultivation method used is extensively described in example 1. Five percent of the protoplasts regenerated to callus and from the positive control it appeared that 15% of the calli had been transformed. In the cocultivation experiments with NTSS12 and NTSS22 $Km^r$calli were obtained. PCR-analysis was performed on chromosomal DNA of pooled tissue of 10 calli (for the method see Lassner et al., 1989). In some calli the transformed T-DNA, which carries the promoterless fusion construct had recombined within the target locus, giving rise to a functional fusion between the rbcS-promoter and the structural part of the NPTII gene. From these calli plants were regenerated and Southern analysis was performed on genomic DNA isolated from these plants. In some of these plants the rbcS-NPTII-part of the T-DNA was found to be correctly integrated at the target locus via homologous recombination.

EXAMPLE

An alternative T-DNA construct to achieve gene targeting to the SSU locus.

Figure 13:
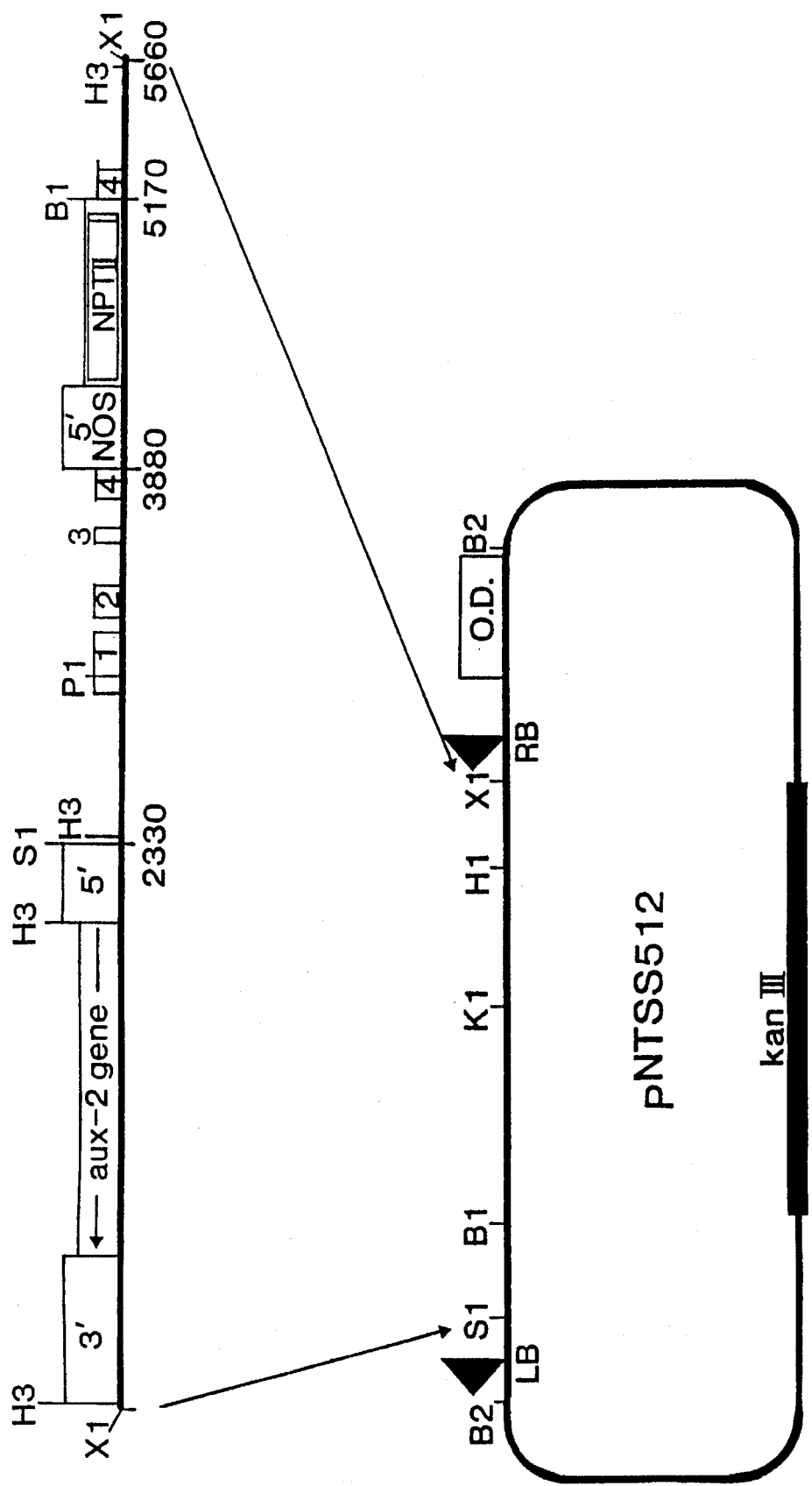
FIG. 13 shows plasmid pNTSS512.

In this part an alternative T-DNA construct to target the SSU locus is described (FIG. 13). In contrast with the SSU-NPTII fusion contructs this new construct does not comprise a translational fusion between the SSU gene and the coding region of the NPTII gene but has the NPTII coding region under the nopaline synthase promoter inserted in the 4th exon of the SSU gene. A small portion of the SSU promoter (±365 bp) is deleted to permit screening for recombinants via PCR. In addition the T-DNA aux-2 gene is introduced into the construct as a negative selection marker to enrich for recombinant calli. The aux-2 gene product converts α-naphtalene acetamide (NAM) to the auxin (NAA). At high concentrations (10–20 mg/l) NAM is capable to promote growth of tobacco cells in auxin-free medium. However, cells that contain the aux-2 gene will efficiently convert NAM to the more potent auxin NAA which is toxic for plant cells at high concentrations (Depicker et al., 1988). Thus, by using auxin-free medium containing NAM at a high concentration it is possible to select for cells, that do not express the aux-2 gene.

A 2.5 Kb HindIII partial of the T-DNA of pTiAch5 (3390 to 5933, Barker, et al., 1983; Gielen et al., 1984) which contains the aux-2 gene was cloned into the HindIII site of pIC20R (Marsch et al., 1984). Sequences upstream of the aux-2 gene comprising the promoter and part of the coding regon of the aux-1 gene were deleted. This was done by digestion with PstI (in the polylinker of pIC), producing blunt ends by using the exonuclease activity of 'Klenow'-polymerase, digestion with HincII (5721, Barker et al., 1983; Gielen et al., 1984) and re-ligation of the plasmid. In this way the promoter sequences of the aux-2 gene were left intact. Subsequently, the aux-2 gene was cloned as a SalI/XhoI fragment into the unique SalI site of pNTSS11B. In the resulting plasmid pNTSS112 the transcription of the aux-2 gene is directed towards the left T-DNA border.

Plasmid pNTSS1 was digested with XhoI followed by a partial digestion with BglII and a 3,9 Kb XhoI/BglII fragment was obtained that contained most of the SSU/NPTII fusion gene exept for 365 bp which were deleted from the 5'end of the SSU promoter region. This fragment was cloned into the pUC derivative pIC19H (Marsch et al., 1984) cut with XhoI and BamHI. The BamHI insertion module containing the NPTII coding region and the OCS terminator was replaced by a BglII/BamHI fragment which consisted of the NPTII coding region behind the NOS promoterregion without the right T-DNA border sequence. The construction of this new insertion module is described below. In the resulting plasmid pNTSS5 the transcription of the NPTII gene from the NOS promoter is directed towards the 3' end of the SSU gene which can serve as terminator of transcription. In this way the OCS terminator can be omitted which results in a reduction of the size of the insertion module. The SalI/BamHI fragment of pNTSS5 was isolated and ligated into the vector part of pNTSS112 cut with SalI and BamHI. Thus, the binary vector pNTSS512 was obtained which contained the alternative targeting construct (see FIG. 13).

For the construction of the new NPTII insertion module the BclI/SmaI fragment of pSDM4 containing the NOS promoter and the restored NPTII coding region was cloned into pIC20H (Marsch et al., 1984) cut with SmaI and BglII. From the resulting plasmid the fragment was excised with XhoI and BamHI and was recloned in pIC19R (Marsch et al., 1984) cut with XhoI and BamHI. Finally, the new NPTII insertion module was introduced as a BglII/BamHI fragment into pNTSS5.

The binary vector pNTSS512 (FIG. 13) was transferred via triparental mating to an Agrobacterium strain that contains the Vir-region on a non-oncogenic helper Ti-plasmid (example 2).

EXAMPLE 14

Transformation with T-DNA construct of plasmid pNTSS512.

Tobacco protoplasts were co-cultivated with Agrobacterium strain NTSS512. To determine the regeneration and transformation frequencies protoplasts were regenerated with or without kanamycin as described in example 1. Non-transformed tobacco cells were cultivated on NAM containing medium to determine the regeneration frequency on this medium. In a larger experiment protoplasts were co-cultivated with strain NTSS512 and grown on auxin-free medium containing kanamycin and 10–20 mg/l NAM. Integration of the T-DNA construct via illegitimate recombination in the genome of the plant cells resulted in kanamycin resistant and aux-2$^+$ cells. Some of these cells were able to grow on NAM-medium because the aux-2 gene was not expressed due to incomplete integration of the T-DNA or inactivation of the gene by methylation. In case the NPTII marker was inserted correctly at the target locus via homologous recombination the aux-2 gene was lost. The resulting cells were resistant to kanamycin and the absence of the aux-2 gene enabled them to grow on auxin-free medium containing a high concentration of NAM.

From the smaller control experiments it was estimated that 5% of the initial protoplasts survived (equal for NAA- and NAM- containing medium) and 15% of the regenerated calli were resistant to kanamycin. In the large targeting experiment the regeneration of protoplasts on NAM-containing medium gave a 10 to 100 fold enrichment for cells that did not express the aux-2 gene. The PCR technique was used to identify the calli obtained through the desired recombination event. Genomic DNA was extracted from pooled tissue of 10 calli (Lassner et al., 1989) and tested in a PCR. The primers used in the reaction respectively annealed in the NPTII coding region and in the upstream region of the SSU promoter that was deleted in T-DNA construct pNTSS512. PCR will only result in amplification of a fragment of expected size if recombination has occurred between incoming T-DNA and target-locus. In fact, in several calli a recombination event was detected. Plants were regenerated from these calli as described and Southern analysis was performed on these plants and on progeny of these plants. In a few plant lines the NPTII module was found to be inserted correctly via homologous recombination at the target locus. It was estimated that the gene targeting frequency ranged from $10^{-4}$ to $10^{-5}$.

Deposition

For the purpose of enablement the following E. coli strains have been deposited at the "Centraal Bureau voor Schimmelcultures" CBS at Baarn, The Netherlands: (strain Dh5α; genotype: F$^-$, endA1, hsdR17 (r$^-$k m$^+$k) supE44, thi-1, lambda$^-$, recA1, gyrA96, relA1, Λ (argFlaczya)U169, phi80dlacz/\M15).

| E. coli strain useful for DH5α with plasmid construct | (Date of Deposition) | (Deposition Number) | |
|---|---|---|---|
| pSDM100 | July 21 1989 | CBS 348.89 | pSDM4 |
| | | | pSDM10 |
| | | | pSDM200/201 |
| | | | pSDM7 |
| pSDM101 | | | |
| pSDM102 | | | |
| | | | pSDM104 |
| pSDM9 | July 21st 1989 | CBS 346.89 | pSDM210/211 |
| pSDM14 | July 21st 1989 | CBS 347.89 | pNTSS11 |
| | | | pNTSS12 |
| | | | pNTSS21 |
| | | | pNTSS22 |
| | | | pNTSS512 |
| PSIC1 | July 21st 1989 | CBS 349.89 | pNTSS11 |
| | | | pNTSS12 |
| | | | pNTSS21 |
| | | | pNTSS22 |
| | | | pNTSS512 |

The Agrobacterium strain LBA4404, which is a good acceptor strain for all binary plant transformation vectors, has already been deposited earlier (Feb. 24th. 1983) and is available via the "Centraal Bureau voor Schimmelcultures" (CBS) at Baarn, The Netherlands, under number CBS 191.83.

Legend
List of symbols and abbreviations used in the figures.

| Symbol | Description |
|---|---|
| ▭ | : A double lined box indicates the coding region of the Km$^r$ and the HM$^r$ gene (NPTTII and HPT). The non-coding region is indicated by a single lined box. |
| 5'NOS◀ | : Fragment comprising the promoter region of the nopaline synthase gene (5'NOS) and the right T-DNA border repeat of the nopaline Ti-plasmid. |
| 3'NOS ■ | : 3' region of the nopaline synthase gene containing the signal for termination of transicription (3'NOS). |
| ▨ 3'OCS ▨ | : 3' region of the octopine synthase gene containing the transcription terminator (3'OCS). |
| 35 SCaMV | : Promoter region of the 35S transcript of CaMV. |
| SUPF ▭ | : 210bp EcoRI fragment containing the *E. coli* supF. |
| ◀ RB | : Right T-DNA border repeat |
| ◀ LB | : Left T-DNA border repeat |
| Hm$^r$ (gene) | : (Gene conferring) hygromycin resistance (to plant cells) |
| Km$^r$ (gene) | : (Gene conferring) kanamycin reisistance (to plant cells) |
| KanIII | : Bacterial kanamycin resistance gene derived from *Streptococcus faecalis* |
| Amp$^r$ | : Bacterial ampicillin resistance gene |
| NPTII | : DNA sequence coding for Neomycin PhosphoTransferase II |
| HPT | : DNA sequence coding for Hygromycin PhosphoTransferase |

LITERATURE

Albright, L. M. et al. J. Bacteriol., 169, 1046–1055. (1987)
Baker, M. D. et al. Proc. Natl. Acad. Sci. US, 85, 6432–6436. (1988)
Bakkeren, G. et al. Cell, 57, 847–857. (1989)
Barker, R. F. Plant Mol. Biol., 2, 335–350. (1983)
Barton, K. A. et al. Methods Enzymol., 101, 527–539. (1983)
Baulcombe, D. C. et al. Nature, 321, 446–449. (1986)
Beck, E. et al. Gene, 19, 327–336. (1982)
Bevan, M. W. et al. Nature, 304, 184–187. (1983)
Bevan, M. W. et al. Nucleic Acids Res., 11 #2, 369–385. (1983b)
Bomhoff, G. et al. Mol. Gen. Genet., 145, 177–181. (1976)
Buchanan-Wollaston, U. et al. Nature, 328, 172–173. (1987)
Capecchi, M. R. Science 2.44, 1288–1292. (1989)
Chiltion, M. D. et al. Nature, 295, 432–434. (1982)
Christie, P. J., J. Bacteriol., 170, 2659–2667. (1988)
Chyi, Y-S. et al. Mol. Gen. Genet., 204, 64–69. (1986)
Citovsky, V. et al. Science, 240, 501–504. (1988)
Citovsky, V. Proc. Natl. Acad. Sci. USA., 86, 1193–1197. (1989)
Crossway, A. et al. Mol. Gen. Genet., 202, 179–185. (1986)
Czerniflofsky, A. P. et al. DNA, 5 #6, 473–482. (1986)
Das, A. Proc. Natl. Acad. Sci. USA, 85, 2909–2913. (1988)
Deroles, S. C. en Gardner, R. C. Plant Mol. Biol., 11, 355–364. (1988)
De Framond, A. J. et al. Bio/Technology, 1, 262–269. (1983)
Deblaere, R. et al. Nucleic Acids Res., 13 #13, 4777–4788. (1985)
Depicker, A. G., Jacobs, A. M. and Van Montagu, M. C., The Plant Cell Reports 7, 63–66. (1988)
Depicker, A. et al. Mol. Gen. Genet., 201, 477–484. (1985)
Ditta, G., Stanfield, S., Corbin, D. and Helinski, D. R., Proc. Nat. Acad. Sci. USA 77, 7347–7351. (1980)
Elzen, P. J. M. van den. Plant Mol. Biol., 5, 149–154. (1985a)
Elzen, P. J. M. van den, et al. Plant Mol. Biol., 5, 149–154. (1983)
Elzen, P. J. M. van den, et al. Plant Mol. Biol., 5, 299–302. (1985)
Figurski, D. H. et al. Proc. Nat. Acad. Sci. USA, 76, 1648–1652. (1979)
Fraley, R. T. et al. Plant Mol. Biol., 3, 371–378. (1984)
Fraley, R. T. et al. Bio/Technology, 3, 629–635. (1985)
Gielen, J. et al. EMBO J., 3, 835–846. (1984)
Gietl, C. et al. Proc. Natl. Acad. Sci. USA, 84, 9006–9010. (1987)
Graves, A. C. F. et al. J. Bacteriol., 169, 1745–1746. (1987)
Graves, A. C. F. et al. Plant Mol. Biol., , 43–50. (1986)
Grimsley, N. et al. Nature, 325, 177–179. (1987)
Gritz, L. et al. Gene, 25, 179–188. (1983)
Haaren, M. J. J. van, et al. Plant Mol. Biol., 8, 95–104. (1987)
Haaren, M. J. J. van, et al. Nucleic Acids Res., 15, 8983–8997. (1986)
Hain, R. et al. Mol. Gen. Genet., 199, 101–168. (1985)
Hernalsteen, J. P. EMBO J. 3, 3039–3041. (1984)
Herrera-Estrella, L. et al. Nature, 303, 203–213. (1983)
Herrera-Estrella, A. C. EMBO J., , 4055–4062. (1988)
Hille, J. et al. J. Bacteriol., 154 #2, 693–701. (1983)
Hille, J. et al. Plant Mol. Biol., 2, 155–163. (1983)
Hoekema, A. et al. Plant Mol. Biol., 5, 85–89. (1985)
Hoekema, A. et al. Nature, 303, 179–180. (1983)
Hoekema, A. et al. J. Bacteriol., 158, 383–385. (1984)
Hoekema, A. et al. EMBO J., 3, 2485–2490. (1984b)
Hooykaas, P. J. J. et al. J. Gen. Microb., 98, 477–484. (1977)
Hooykaas-Van Slogteren, G. M. S. et al. Nature, 311, 763–764. (1984)
Hooykaas, P. J. J. et al. J. Bacteriol., 143, 1295–1306. (1980)
Horsch, R. B. et al. Science, 277, 1229–1231. (1985)
Jefferson, R. A. EMBO J., 4, 25–32. (1987)
Joos, H. et al. EMBO J., 2, 2151–2160. (1983)
Kerr, A. et al. Physiol. Plant Pathol., 9, 205–221. (1976)
Kim, H. S. en Smithies. Nucleic Acids Res., 8887–8903. (1988)
Klee, H, et al. Ann. Rev. Plant Phys., 38, 467–486. (1987)
Klein et al. Nature, 327, 70–73, (1987)
Krens, F. A. et al. Nature, 296, 72–74. (1982)
Kucherlapati, R. S. et al., Proc. Natl. Acad. Sci. USA, 81, 3153–3157. (1984)
Lassner, N. W. Plant Mol. Biol., , 116–128. (1989)
Maniatis, T. et al. Mol. Cloning, a laboratory manual. (1982)
Marsh, J. L. Gene, 32, 481–485. (1984)
Marton, L. et al. Nature, 277, 129–131. (1979)
Mazur, B. et al. Nucleic Acids Res., 13, 2373–2386. (1985)
Melchers, L. S. et al. Oxford Surveys of Plant Mol. and Cell Biol., 4, 167–220. (1987)

Messing, J. et al. Methods Enzymol., 101, 20–79. (1983)
Mettler, I. J. Plant Mol. Biol., 5, 346–349. (1987)
Muller, J. F. et al. Physiol. Plant, 57, 37–41. (1983)
Murashige, T. et al. Physiol. Plant, 15, 473–497. (1962)
Nagy, J. I. et al. Pflanzenphysiol., 78, 453–455. (1976)
Negrutiu, I. et al. Plant Mol. Biol., 8, 363–373. (1987)
Ooms, G. et al. Gene, 14, 33–50. (1981)
Ooms, G. et al. Plasmid, 7, 15–29. (1982)
Orr-Weaver, T. L., et al. Proc. Natl. Acad. Sci. USA, 78, 6354–6358. (1981)
Paszkowski, J. et al. Plant Mol. Biol., juni, 10–19. (1987)
Paszkowski, J. EMBO J., 7, 4021–4026. (1988)
Peerbolte, R. et al. Plant Mol. Biol., 5, 234–246. (1985)
Peralta, E. G. et al. EMBO J., 5, 1137–1142. (1986)
Peralta, E. G. et al. Proc. Natl. Acad. Sci. USA, 82, 5112–5116. (1985)
Platt, S. G. et al. Analytical Biochem., 162, 529–535. (1987)
Ruvkun, G. B. et al. Nature, 286, 85–88. (1981)
Saiki, R. K. Science, 239, 487–491. (1988)
Sanger, F. et al. Proc. Natl. Acad. Sci. USA, 74 #12, 5463–5467. (1977)
Schreier, P. H. et al. EMBO J., 4, 25–32. (1985)
Seed, B. Nucleic Acids Res., 8, 2427–2445. (1983)
Sen, P. et al. J. Bacteriol., 2573–2580. (1989)
Shaw, C. H. et al. Nucleic Acids Res., 12, 6031–6041. (1984)
Sheerman, S. et al. Plant Cell Reports, 7, 13–16. (1988)
Shillito, R. D. et al, Bio/Technology, 3, 1099–1102. (1985)
Slightom, J. L. et al. EMBO J., 4, 3069–3077. (1985)
Smithies, O. et al. Nature, 317, 230–234. (1985)
Song, K-Y et al, Proc. Natl. Acad. Sci. USA, 84, 6820–6824. (1987)
Southern, E., J. Mol. Biol., 98, 503. (1975)
Spielmann, A. et al. MGG, 205, 34–41. (1986)
Stachel, S. E. et al, Nature, 322, 706–711. (1986)
Stachel, S. E, et al. EMBO J. 6, 857–863. (1987)
Thomas, K. R. et al. Cell, 51, 503–512. (1987)
Thomashow, M. F. et al. Cell, 19, 729–739. (1980)
Ulian, E. C. et al. In vitro Cellular and Developmental Biology, 24, 951–954. (1988)
Veen, R. J. N. van, et al. Thesis: Stategies of Bacteria in their interaction with plants; Analogies and Specialization., 79–91. (Leiden, The Netherlands, 1988)
Wallroth, M. et al. Mol. Gen. Genet., 202, 6–15. (1986)
Wang, K. et al. Mol, Gen. Genet., 210, 236–346. (1987)
Wang, K. et al. Cell, 38, 455–462. (1984)
Ward, E. R. Science, 242, 927–930. (1988)
Willmitzer, L. et al. Mol. Gen. Genet., 186, 16–22. (1982)
Willmitzer, L. et al. EMBO J., 1, 139–146. (1982)
Wirtz, U. et al. DNA, 6, 245–255. (1987)
Yadav, N. S. et al. Proc. Natl. Acad. Sci. USA, 79, 6322–6326. (1982)
Young, C. J. Bacteriol., 170, 3367–3374. (1988)
Zambryski, P. et al. J. Mol. App. Genet., 1, 361–370. (1982)
Zambryski, P. et al. EMBO J., 2, 2143–2150. (1983)
Zimmer, A. en Guss. Nature, 338, 150–153. (1989)

We claim:

1. A process for introducing a defined DNA sequence in a selected target locus of a nuclear plant cell genome by integrating at least a part of a recombinant DNA into said genome through homologous recombination at the target locus, comprising the steps of:

a) coincubating plant protoplasts or plant cells under transforming conditions, with a strain of the genus Agrobacterium capable of T-region transfer and containing a plant transformation vector which comprises recombinant DNA of the formula:

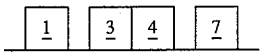

wherein boxes 1 and 7 are T-DNA border sequences, and wherein one of box 1 or 7 may be absent; and wherein box 3 comprises a DNA sequence sufficiently homologous to a DNA sequence inside the target locus and sufficiently long to promote homologous recombination; and wherein box 4 comprises a DNA sequence not homologous to sequences occurring in the target locus; and wherein the lines connecting the boxes shown may comprise any number of nucleotides or basepairs, and b) identifying protoplasts or cells that have obtained the said defined DNA sequence in their genomes at said target locus.

2. The process of claim 1 wherein the recombinant DNA has the formula:

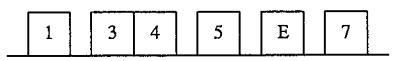

wherein box 5 comprises an expression cassette for a positive selection gene functional in said cell; and wherein box E comprises a DNA sequence sufficiently homologous to DNA sequences inside or adjacent to the target locus to promote homologous recombination.

3. The process according to claim 2, wherein the positive selection gene is selected from the group consisting of the nptII gene, the hpt-gene and the Als gene.

4. A process for introducing a defined mutation in a selected target locus of a nuclear plant cell genome by integrating at least a part of a recombinant DNA into said genome through homologous recombination at the target locus, comprising the steps of:

a) coincubating plant protoplasts or plant cells under transforming conditions, with a strain of the genus Agrobacterium capable of T-region transfer and containing a plant transformation vector which comprises recombinant DNA of the formula:

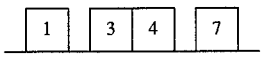

wherein boxes 1 and 7 are T-DNA border sequences, and wherein one of box 1 or 7 may be absent; and wherein box 3 comprises a DNA sequence sufficiently homologous to a DNA sequence inside the target locus and sufficiently long to promote homologous recombination; and wherein box 4 comprises a DNA sequence sufficiently homologous to promote homologous recombination with a corresponding sequence in the target locus and wherein box (4) comprises the said defined mutation; and wherein the lines connecting the boxes shown may comprise any number of nucleotides or basepairs, and b) identifying protoplasts or cells that have obtained the said defined mutation in their genome at the said target locus.

5. The process of claim 4 wherein said recombinant DNA has the formula:

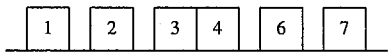

wherein each of boxes 2 and 6 comprises an expression cassette for a negative selection gene functional in said plant cell; and wherein one of box 2 and 6 may be absent.

6. The process of claim 5, wherein said recombinant DNA has the formula:

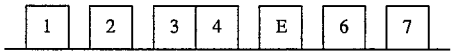

wherein box E comprises a DNA sequence sufficiently homologous to DNA inside or adjacent to the target locus to promote homologous recombination.

7. The process of claim 5 wherein said recombinant DNA has the formula:

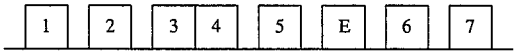

wherein box 5 comprises an expression cassette for a positive selection gene which is functional in said plant cell.

8. The process according to claim 7, wherein the positive selection gene is selected from the group consisting of the nptII gene, the hpt-gene and the Als-gene.

9. A recombinant DNA capable of introducing a defined mutation in a selected target locus of a nuclear plant cell genome through homologous recombination at the target locus, which recombinant DNA has the formula:

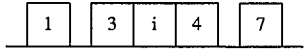

wherein box i comprises the said defined mutation; and wherein boxes 1 and 7 are T-DNA border sequences, and wherein one of box 1 or 7 may be absent; and wherein each of boxes 3 and 4 individually is a DNA sequence sufficiently homologous to a DNA sequence inside the target locus and sufficiently long to promote homologous recombination; and wherein the DNA sequences of the boxes 3 and 4 have the same 5'-to-3' orientation, but wherein said boxes 3 and 4 are rearranged with respect to the homologous sequences in the target locus.

10. The recombinant DNA of claim 9 which has the formula:

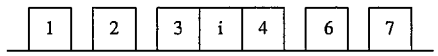

wherein each of boxes 2 and 6 comprise an expression cassette for a negative selection gene functional in said plant cell; and wherein one of box 2 and 6 may be absent.

11. The recombinant DNA of claim 10 wherein said negative selection gene is selected from the group consisting of the aux-2 gene, the cytochrome p450 gene, the Adh-gene, and the tk-gene.

12. A replicon suitable for cloning in bacteria containing the recombinant DNA of claim 10.

13. A bacterium containing the replicon of claim 12.

14. A plant transformation vector which comprises the recombinant DNA of claim 10.

15. A plant transformation vector which comprises the recombinant DNA of claim 11.

16. A bacterial strain of the genus Agrobacterium capable of DNA transfer to plant cells which contains the plant transformation vector of claim 14.

17. A bacterial strain of the genus Agrobacterium capable of DNA transfer to plant cells which contains the plant transformation vector of claim 15.

18. A process for the preparation of a plant cell containing a defined mutation at a selected target locus of the nuclear genome through homologous recombination with a recombinant DNA containing said mutation, comprising the steps of, a) coincubating plant protoplasts or plant cells under transforming conditions, with a strain of the genus Agrobacterium according to claim 16, and b) identifying a protoplast or cell that has obtained the said defined mutation.

19. A process for the preparation of a plant cell containing a defined mutation at a selected target locus of the genome, via homologous recombination, comprising the steps of:

(a) coincubating plant protoplasts or plant cells under transforming conditions, with a strain of the genus Agrobacterium according to claim 17, (b) selecting or enriching for cells which do not express any of the negative marker genes, under conditions allowing for selection, and (c) identifying a protoplast or cell that has obtained the defined mutation in its genome at the target locus.

* * * * *